US008685661B2

(12) United States Patent
Zhao et al.

(10) Patent No.: US 8,685,661 B2
(45) Date of Patent: *Apr. 1, 2014

(54) REAGENT AND KIT FOR CLASSIFYING AND COUNTING LEUKOCYTES, THE PREPARATION THEREOF, AND PROCESS FOR CLASSIFYING AND COUNTING LEUKOCYTES

(75) Inventors: Yang Zhao, Nanshan Shenzhen (CN); Ting Lei, Nanshan Shenzhen (CN); Yumei Zhao, Nanshan Shenzhen (CN); Bing Xu, Nanshan Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 5 days.

This patent is subject to a terminal disclaimer.

(21) Appl. No.: 12/843,671

(22) Filed: Jul. 26, 2010

(65) Prior Publication Data
US 2011/0027788 A1 Feb. 3, 2011

(30) Foreign Application Priority Data

Jul. 31, 2009 (CN) .......................... 2009 1 0109215

(51) Int. Cl.
*G01N 33/49* (2006.01)
*A61K 31/427* (2006.01)
(52) U.S. Cl.
USPC .......................................... 435/7.24; 514/366
(58) Field of Classification Search
USPC ........................................................ 546/122
See application file for complete search history.

(56) References Cited

U.S. PATENT DOCUMENTS

| 3,883,274 | A | 5/1975 | Vuaille |
|---|---|---|---|
| 4,122,348 | A | 10/1978 | Bruck |
| 4,146,604 | A | 3/1979 | Kleinerman |
| 4,286,963 | A | 9/1981 | Ledis et al. |
| 4,325,706 | A | 4/1982 | Gershman et al. |
| 4,332,785 | A | 6/1982 | Allen et al. |
| 4,336,029 | A | 6/1982 | Natale |
| 4,414,325 | A | 11/1983 | Masuda et al. |
| 4,447,547 | A | 5/1984 | Allen et al. |
| 4,485,175 | A | 11/1984 | Ledis et al. |
| 4,528,274 | A | 7/1985 | Carter et al. |
| 4,529,705 | A | 7/1985 | Larsen |
| 4,544,546 | A | 10/1985 | Wang et al. |
| 4,571,388 | A | 2/1986 | O'Connell et al. |
| 4,596,035 | A | 6/1986 | Gershman et al. |
| 4,617,275 | A | 10/1986 | Matsuda et al. |
| 4,637,986 | A | 1/1987 | Brown et al. |
| 4,707,451 | A | 11/1987 | Sage et al. |
| 4,745,071 | A | 5/1988 | Lapicola et al. |
| 4,751,179 | A | 6/1988 | Ledis et al. |
| 4,822,745 | A | 4/1989 | Burns et al. |
| 4,882,284 | A | 11/1989 | Kirchanski et al. |
| 4,883,867 | A | 11/1989 | Lee et al. |
| 4,933,293 | A | 6/1990 | Kuroda et al. |
| 4,957,870 | A | 9/1990 | Lee et al. |
| 4,971,917 | A | 11/1990 | Kuroda |
| 4,978,624 | A | 12/1990 | Cremins et al. |
| 4,981,803 | A | 1/1991 | Kuroda |
| 4,985,174 | A | 1/1991 | Kuroda et al. |
| 5,039,613 | A | 8/1991 | Matsuda et al. |
| 5,075,556 | A | 12/1991 | Fan et al. |
| 5,116,539 | A | 5/1992 | Hamaguchi et al. |
| 5,155,044 | A | 10/1992 | Ledis et al. |
| 5,175,109 | A | 12/1992 | Sakata et al. |
| 5,179,026 | A | 1/1993 | Matsuda et al. |
| 5,180,677 | A | 1/1993 | Di Ianni et al. |
| 5,188,935 | A | 2/1993 | Leif et al. |
| 5,227,304 | A | 7/1993 | Wong |
| 5,232,857 | A | 8/1993 | Lefevre et al. |
| 5,242,832 | A | 9/1993 | Sakata |
| 5,250,437 | A | 10/1993 | Toda et al. |
| 5,264,369 | A | 11/1993 | Sakata et al. |
| 5,284,771 | A | 2/1994 | Fan et al. |
| 5,316,725 | A | 5/1994 | Carver et al. |
| 5,316,951 | A | 5/1994 | Carver et al. |
| 5,321,130 | A | 6/1994 | Yue et al. |
| 5,350,695 | A | 9/1994 | Colella et al. |
| 5,360,739 | A | 11/1994 | Fan et al. |

(Continued)

FOREIGN PATENT DOCUMENTS

| CN | 1101980 | 4/1995 |
|---|---|---|
| CN | 1101982 | 4/1995 |

(Continued)

OTHER PUBLICATIONS

Nakamura, I. et al. Transition-Metal-Catalyzed Reactions in Heterocyclic Synthesis. Chem. Rev. 2004, vol. 104, p. 2127.*
Chattopadhyay, SK. et al. Formation of medium-ring heterocycles by diene and enyne metathesis. Tetrahedron. 2007, vol. 63, p. 3919.*
Dorwold, FZ. Side Reactions in Organic Synthesis. Wiley. 2005, preface.*
Notice of Allowance in U.S. Appl. No. 11/967,897 dated Feb. 9, 2011.
Netzel, T. et al., "Base-Content Dependence of Emission Enhancements, Quantum Yields, and Lifetimes for Cyanine Dyes Bound to Double Strand DNA: Photophysical Properties of Monomeric and Bichromophoric DNA Stains". 1995, J. Phys. Chem., 99, 17936-179474.

(Continued)

*Primary Examiner* — Wu-Cheng Winston Shen
*Assistant Examiner* — Ana Z Muresan
(74) *Attorney, Agent, or Firm* — Kory D. Christensen; Stoel Rives LLP

(57) ABSTRACT

A reagent for classifying and counting leukocytes containing (1) a cyanine fluorescent dye; and (2) a glycoside compound; a reagent kit containing the reagent for classifying and counting leukocytes as well as its preparation process; and a process for classifying and counting blood cells using the reagent or kit are provided. Using the reagent, kit and/or process provided, leukocytes can be classified and counted in four groups with a high degree of differentiation and a better classification among each subpopulation of leukocytes, especially in that it successfully addresses the indistinct classification between lymphocytes and monocytes and between the eosinophils and neutrophils in a scattergram.

12 Claims, 12 Drawing Sheets

(56) References Cited

U.S. PATENT DOCUMENTS

| | | | |
|---|---|---|---|
| 5,389,549 A | 2/1995 | Hamaguchi et al. | |
| 5,411,891 A | 5/1995 | Fan et al. | |
| 5,413,938 A | 5/1995 | Tsujino et al. | |
| 5,438,003 A | 8/1995 | Colella et al. | |
| 5,486,477 A | 1/1996 | Carver et al. | |
| 5,492,833 A | 2/1996 | Rodriguez et al. | |
| 5,496,734 A | 3/1996 | Sakata | |
| 5,510,267 A | 4/1996 | Marshall | |
| 5,516,695 A | 5/1996 | Kim et al. | |
| 5,518,928 A | 5/1996 | Cremins et al. | |
| 5,538,893 A * | 7/1996 | Sakata et al. | 436/10 |
| 5,559,037 A | 9/1996 | Kim et al. | |
| 5,563,070 A | 10/1996 | Yamamoto et al. | |
| 5,616,501 A | 4/1997 | Rodriguez et al. | |
| 5,618,733 A | 4/1997 | Sakata et al. | |
| 5,633,167 A | 5/1997 | Fan et al. | |
| 5,639,630 A | 6/1997 | Malin et al. | |
| 5,639,666 A | 6/1997 | Shenkin et al. | |
| 5,656,449 A | 8/1997 | Yue | |
| 5,677,183 A | 10/1997 | Takarada et al. | |
| 5,686,308 A | 11/1997 | Li et al. | |
| 5,691,204 A | 11/1997 | Kim et al. | |
| 5,731,206 A | 3/1998 | Ledis et al. | |
| 5,733,784 A | 3/1998 | Studholme et al. | |
| 5,747,343 A | 5/1998 | Tsuchiya et al. | |
| 5,763,280 A | 6/1998 | Li et al. | |
| 5,773,299 A | 6/1998 | Kim et al. | |
| 5,786,224 A | 7/1998 | Li et al. | |
| 5,817,518 A | 10/1998 | Li et al. | |
| 5,821,127 A | 10/1998 | Akai et al. | |
| 5,821,128 A | 10/1998 | Provost | |
| 5,840,515 A | 11/1998 | Provost | |
| 5,843,608 A | 12/1998 | Li et al. | |
| 5,858,667 A | 1/1999 | Dertinger et al. | |
| 5,874,311 A | 2/1999 | Li et al. | |
| 5,879,900 A | 3/1999 | Kim et al. | |
| 5,882,934 A | 3/1999 | Li et al. | |
| 5,891,731 A | 4/1999 | Akai et al. | |
| 5,928,949 A | 7/1999 | Sakata et al. | |
| 5,958,776 A | 9/1999 | Sakata et al. | |
| 5,968,832 A | 10/1999 | Uchihashi et al. | |
| 5,994,089 A | 11/1999 | Siiman et al. | |
| 5,994,138 A | 11/1999 | Veriac | |
| 6,004,816 A | 12/1999 | Mizukami et al. | |
| 6,060,322 A | 5/2000 | Horton et al. | |
| 6,100,038 A | 8/2000 | Dertinger et al. | |
| 6,114,130 A * | 9/2000 | Veriac et al. | 435/7.24 |
| 6,114,173 A | 9/2000 | Zelmanovic et al. | |
| 6,197,593 B1 | 3/2001 | Deka et al. | |
| 6,245,499 B1 | 6/2001 | Suzuki et al. | |
| 6,248,319 B1 | 6/2001 | Zsebo et al. | |
| 6,271,035 B1 | 8/2001 | Deka et al. | |
| 6,287,791 B1 | 9/2001 | Terstappen et al. | |
| 6,350,613 B1 | 2/2002 | Wardlaw et al. | |
| 6,368,864 B1 | 4/2002 | Deka et al. | |
| 6,495,692 B1 | 12/2002 | Wang et al. | |
| 6,524,858 B1 | 2/2003 | Zelmanovic et al. | |
| 6,551,831 B2 | 4/2003 | Gupta et al. | |
| RE38,131 E | 6/2003 | Uchihashi et al. | |
| 6,630,990 B2 | 10/2003 | van't Dever et al. | |
| 6,632,676 B1 | 10/2003 | Crews et al. | |
| 6,664,110 B1 | 12/2003 | Tsuji et al. | |
| 6,794,152 B2 | 9/2004 | Ryan et al. | |
| 6,869,798 B2 | 3/2005 | Crews et al. | |
| 6,900,023 B1 | 5/2005 | Houwen et al. | |
| 6,955,872 B2 | 10/2005 | Maples et al. | |
| 6,977,156 B2 | 12/2005 | Ryan et al. | |
| 7,083,982 B2 | 8/2006 | Wang et al. | |
| 7,235,404 B2 | 6/2007 | Lang et al. | |
| 7,247,484 B2 | 7/2007 | Wu et al. | |
| 7,300,797 B2 | 11/2007 | van Agthoven et al. | |
| 7,405,082 B2 | 7/2008 | Mizukami et al. | |
| 7,449,337 B2 | 11/2008 | Deka et al. | |
| 7,465,584 B2 | 12/2008 | Matsumoto et al. | |
| 7,598,385 B2 * | 10/2009 | Peng et al. | 546/165 |
| 7,709,653 B2 | 5/2010 | Jianhui | |
| 7,960,099 B2 * | 6/2011 | Xu et al. | 435/2 |
| 8,067,602 B2 * | 11/2011 | Shao | 546/165 |
| 8,367,358 B2 * | 2/2013 | Ting et al. | 435/14 |
| 2002/0182623 A1 | 12/2002 | Lefevre et al. | |
| 2003/0145394 A1 | 8/2003 | Wang et al. | |
| 2004/0241769 A1 | 12/2004 | Crews et al. | |
| 2005/0202400 A1 | 9/2005 | Tsuji et al. | |
| 2005/0272026 A1 | 12/2005 | Oguni | |
| 2006/0177347 A1 | 8/2006 | Larsen et al. | |
| 2007/0111276 A1 | 5/2007 | Lefevre et al. | |
| 2007/0178597 A1 | 8/2007 | Tsuji et al. | |
| 2008/0026475 A1 | 1/2008 | van Agthoven et al. | |
| 2008/0131898 A1 | 6/2008 | Tsuji et al. | |
| 2008/0176274 A1 | 7/2008 | Tsuji et al. | |
| 2009/0017441 A1 * | 1/2009 | Peng et al. | 435/4 |
| 2009/0023129 A1 * | 1/2009 | Xu et al. | 435/2 |
| 2009/0176270 A1 | 7/2009 | Shao | |
| 2009/0305285 A1 | 12/2009 | Jianhui | |
| 2010/0151509 A1 | 6/2010 | Ting et al. | |

FOREIGN PATENT DOCUMENTS

| | | |
|---|---|---|
| CN | 1202621 | 12/1998 |
| CN | 1149397 | 5/2004 |
| EP | 0548983 | 6/1993 |
| EP | 0794435 | 9/1997 |
| WO | WO 97/17471 A1 * | 5/1997 |
| WO | WO9717471 | 5/1997 |
| WO | WO03104771 | 12/2003 |

OTHER PUBLICATIONS

Office Action dated May 10, 2011 for U.S. Appl. No. 12/334,274.

Notice of Allowance in U.S. Appl. No. 11/967,897 dated Mar. 10, 2011.

U.S. Appl. No. 12/580,474, filed Oct. 16, 2009, Yuji.

Notice of Allowance in U.S. Appl. No. 11/967,991 dated Aug. 7, 2009.

Jason A. Bordelon et al., "Viscometry and Atomic Force Microscopy Studies of the Interactions of a Dimeric Cyanine Dye with DNA", J. Phys. Chem. B 2002, 106, 4838-4843.

Alexandre Furstenberg et al., "Ultrafast Excited-State Dynamics of DNA Fluorescent Intercalators: New Insight into the Fluorescence Enhancement Mechanism", J. Am. Chem. Soc. 2006, 128, 7661-7669.

L.G.S. Brooker et al., "Absorption of Unsymmetrical Carbocyanines", J. Amer. Chem. Soc., 1945, 67, 1889-93.

Notice of Allowance in U.S. Appl. No. 12/482,335 dated Feb. 22, 2010.

Stephen J. Mason et al., "Solid-Phase Catch, Activate, and Release Synthesis of Cyanine Dyes", American Chemical Society Organic Letters 2002, vol. 4 No. 24, pp. 4261-4264.

Kristine M. Sovenyhazy et al., "Spectroscopic Studies of the Multiple Binding Modes of a Trimethine-Bridged Cyanine Dye with DNA", Nucleic Acids Research, vol. 31 No. 10, 2561-2569, 2003.

Kristine M. Sovenyhazy et al., "Spectroscopic Studies of the Multiple Binding Modes of a Trimethine-Bridged Cyanine Dye with DNA", Nucleic Acids Research, vol. 31 No. 10, 2561-2569, Received Feb. 5, 2003, Revised and Accepted Mar. 24, 2003.

Fei, X. et al., "Solid-Phase Synthesis and Modification of Thiazole Orange and its Derivatives and Their Spectral Properties". Journal of Combinatorial Chemistry, vol. 9 (6), p. 945 (last 2 paragraphs), 2007.

Office Action dated Oct. 25, 2011 for U.S. Appl. No. 12/580,474.

* cited by examiner

US 8,685,661 B2

REAGENT AND KIT FOR CLASSIFYING AND COUNTING LEUKOCYTES, THE PREPARATION THEREOF, AND PROCESS FOR CLASSIFYING AND COUNTING LEUKOCYTES

RELATED APPLICATIONS

This application claims priority to Chinese Patent Application No. 200910109215.6, filed on Jul. 31, 2009, for "REAGENT AND KIT FOR CLASSIFYING AND COUNTING LEUKOCYTES, THE PREPARATION THEREOF, AND PROCESS FOR CLASSIFYING AND COUNTING LEUKOCYTES," the disclosure of which is fully incorporated herein by reference.

TECHNICAL FIELD

The present disclosure relates to a reagent and a process for classifying and counting blood cells. Specifically, the present disclosure relates to a reagent for classifying and counting leukocytes, a kit containing said reagent and preparation thereof, and a process for classifying and counting leukocytes using the reagent and/or the kit.

DETAILED DESCRIPTION

Figure 1:
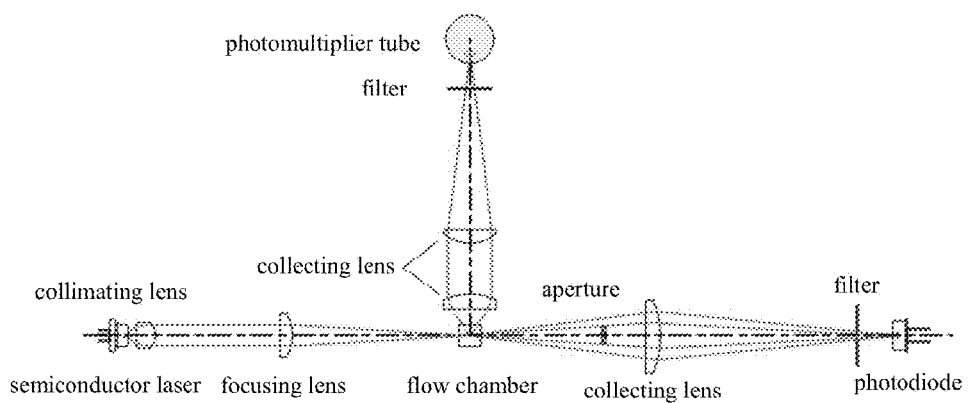
FIG. 1 is a scheme illustrating the optical system of a flow cytometer.

Blood cells can generally be divided into three categories: erythrocytes, leukocytes and platelets, wherein leukocytes can be further divided into five subpopulations: lymphocytes, monocytes, neutrophils, eosinophils, and basophils. Accurate classification of leukocytes into different subpopulations is of great significance for diagnosis or research purposes in the field of biological analysis, especially in the field of clinical assays, since changes in the content of each subpopulation of leukocytes are used as key indicators in clinical diagnosis and treatment. For example, acute bacterial infection results in an increase of neutrophils, while parasitic infections and allergic diseases result in an increase of eosinophils.

So far, a number of reagents and processes for classifying and counting leukocytes have been reported. Basically, erythrocytes and platelets are lysed with a hemolytic agent before the leukocytes are classified and counted. Quaternary ammonium or pyridinium compounds are commonly used as cationic surfactants for lysing erythrocytes before classification of leukocytes. Compared with anionic and nonionic surfactants, quaternary ammonium surfactants are of higher toxicity. In addition, quaternary ammonium surfactants may inhibit bacteria and therefore can be damaging when they come into contact with environmental microorganisms.

In addition to cationic surfactants, types of glycosides called "saponins", which are known as natural surfactants, are also used in the classification of leukocytes, since they have hemolytic activity.

U.S. Pat. No. 5,155,044 discloses a two-step process for classifying leukocytes. A reagent system for chemical treatment of whole blood comprising a lytic reagent and a quench reagent is used in the process. The lytic reagent comprises acids or a mixture of acids and saponins. The acid is the essential component in the process, while the saponins are used for more complete lysis of erythrocytes in order to avoid their interference in the process.

U.S. Pat. No. 4,751,179 discloses a reagent system for classifying leukocytes and a process for differentiating leukocytes with an automated cell counting instrument. The reagent system comprises a reagent comprising saponins, and a reagent for fixation.

U.S. Pat. No. 5,840,515 discloses a method for differentiating leukocytes in a blood sample comprising the following steps: (1) lysing of the erythrocytes with a hemolytic agent containing saponins while maintaining leukocyte integrity, (2) determining the endpoint of lysis, and (3) adding a quenching agent to stop lysis after the reaction threshold is reached.

U.S. Pat. No. 6,632,676 discloses a method for classifying leukocytes into five groups. Two reagents are used in the method; one is a hemolytic agent comprising saponin, and the other is a quenching agent containing a buffering means to quench the hemolysis reaction of the saponin.

U.S. Pat. No. 6,114,130 discloses a reagent for classifying leukocytes into four groups. The reagent comprises a cationic surfactant, a glycoside (specifically a saponin), and at least one inorganic salt and a buffer to adjust the pH of the reagent.

Most of the above-mentioned prior art for classifying leukocytes with a saponin nonionic surfactant involve two or three steps and require two or more reagents, which increases both the complexity of instrument design and the cost of manufacture. In addition, the classification of leukocytes using the prior art with saponins is not satisfactory, especially in that the classification between the sub-populations of lymphocytes and monocytes is not clear.

In one aspect, the present disclosure relates to a reagent for classifying and counting leukocytes, which comprises:
(1) a cyanine fluorescent dye; and
(2) a glycoside compound.

In one embodiment, the glycoside compound is a saponin or an alkyl glycoside compound.

In one embodiment, the cyanine fluorescent dye is a compound having the general formula (I) or (II) or a combination thereof:

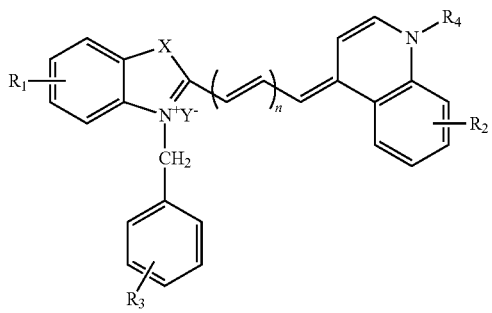

formula (I)

wherein
n is 1, 2 or 3;
X is $C(CH_3)_2$, O, S or Se;
$R_1$ and $R_2$ are each independently selected from H, $C_{1-18}$alkyl, $C_{1-6}$alkyl-$OR_5$ and halogen;
$R_3$ is H, $C_{1-18}$alkyl, $OR_5$, $C_{1-6}$alkyl-$OR_5$, $COOR_5$, $NO_2$, CN or halogen;
$R_4$ is $C_{1-18}$alkyl, $C_{1-6}$alkyl-$OR_5$, benzyl or halogen, wherein said benzyl is optionally substituted with one or more substituents independently selected from the group consisting of halogen, hydroxyl, sulfhydryl, cyano, nitro, alkyl, aryl, alkoxy, heterocyclyl, haloalkyl, amino, alkylamino, amido, and carboxyl;

$R_5$ is H or $C_{1-18}$alkyl; and
$Y^-$ is an anion;

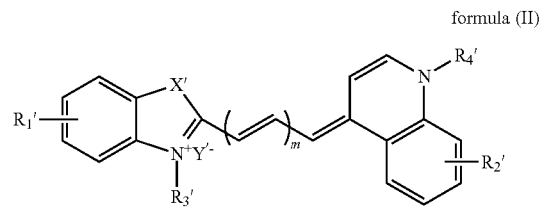

formula (II)

m is 1, 2 or 3;
X' is $C(CH_3)_2$, O, S or Se;
$R_1'$ and $R_2'$ are each independently selected from H, OH, $C_{1-18}$alkyl, $C_{1-6}$alkyl-$OR_5'$, $C_{1-18}$alkylsulfonate, phenyl and halogen;
$R_3'$ and $R_4'$ are each independently selected from $C_{1-18}$alkyl-$COOR_6'$, $C_{1-18}$alkyl-$OR_6'$ or benzyl, wherein said benzyl is optionally substituted with one or more substituents independently selected from the group consisting of halogen, hydroxyl, sulfhydryl, cyano, nitro, alkyl, aryl, alkoxy, heterocyclyl, haloalkyl, amino, alkylamino, amido, and carboxyl, provided that $R_3'$ and $R_4'$ are not simultaneously benzyl, and $R_4'$ is not $C_{1-18}$alkyl-$OR_6'$ when $R_3'$ is benzyl.
$R_5'$ is H or $C_{1-18}$alkyl;
$R_6'$ is H, phenyl or $C_{1-18}$alkyl, wherein said phenyl is optionally substituted with one or more substituents independently selected from the group consisting of halogen, hydroxyl, sulfhydryl, cyano, nitro, alkyl, aryl, alkoxy, heterocyclyl, haloalkyl, amino, alkylamino, amido, and carboxyl; and
$Y'^-$ is an anion.

Optionally, the reagent of the present disclosure may further comprise a second nonionic surfactant having the general formula (III):

$$R_1—R_2—(CH_2CH_2O)_n—H$$

formula (III)

wherein
$R_1$ is a $C_{8-23}$alkyl or $C_{8-23}$alkenyl, and includes a straight-chain alkyl selected from octyl, decyl, lauryl, myristyl, cetyl and stearyl. Some embodiments include a straight-chain alkyl selected from lauryl, myristyl and cetyl;
$R_2$ is —O—,

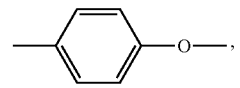

or —COO—; and
n is an integer from 10 to 30.

Optionally, the reagent of the present disclosure may further comprise an anionic compound selected from an acid carrying one or more carboxyl or sulfonate groups and salts thereof.

Optionally, the reagent of the present disclosure may further comprise an alcohol.

Optionally, the reagent of the present disclosure may further comprise an additive selected from a preservative, a metal chelating agent, a buffering agent, and osmotic regulating agent.

In another aspect, the present disclosure relates to a reagent kit for classifying and counting leukocytes. The kit comprises the reagent for classifying and counting leukocytes disclosed herein, and all components of the reagent can be provided in the form of a single package, or alternatively in the form of two or more separate packages, with the cyanine fluorescent dye packaged separately from the other components.

In another aspect, the present disclosure relates to a process for preparing a reagent kit for classifying and counting leukocytes, wherein the process comprises:
- dissolving an amount of each component of the present reagent into water, adjusting the pH of the solution and diluting to a certain volume, and packaging it in the form of a kit; or
- dissolving an amount of cyanine fluorescent dye of the present reagent into an organic solvent, diluting to a certain volume and packaging; dissolving an amount of each of the other components of the present reagent into water separately or together, adjusting the pH of the solution and diluting to a certain volume, and packaging; packing the two separate packages in the form of a kit.

In still another aspect, the present disclosure relates to a process for classifying and counting leukocytes, wherein the process comprises the following steps:
(1) mixing a blood sample with the present reagent or reagent kit according to the present disclosure for a period of time to lyse erythrocytes and platelets and damage leukocytes to provide morphological changes to each subpopulation of leukocytes, and labeling the nucleic acids in the leukocytes with a fluorescent dye;
(2) classifying the leukocytes into at least four groups, three groups corresponding to monocytes, lymphocytes and eosinophils and one group corresponding to neutrophils and basophils, by measuring any two of the following: the information on side-scattered light intensity, the information on forward-scattered light intensity, and the information on side fluorescence intensity, preferably by measuring the information on side-scattered light intensity and the side fluorescence intensity; and then counting the leukocytes in each category.

The glycosidic nonionic surfactant used in the present reagent for classifying and counting leukocytes provides the following advantages: it is readily available from a wide variety of sources; it is non-toxic, non-irritative, and mild to the human skin; and it is rapidly and completely biodegradable, and available from renewable resources. In addition, the reagent for classifying and counting leukocytes has a neutral pH value, which reduces the corrosion to the instrument. The present process for classifying leukocytes is a one-step process, and thus provides the advantages of a shorter reaction time, a more rapid reaction speed, and a simpler instrument compared to a two-step method, which thereby reduces the production costs. The scattergram obtained by the present reagent and process for classifying and counting leukocytes has a high degree of cellular differentiation and a better classification among each subpopulation of leukocytes, especially in that it successfully addresses the indistinct classification between lymphocytes and monocytes and the undesired closeness between eosinophils and neutrophils in the scattergram. The classification and count resulting from the present disclosure has a good correlation with the one obtained by conventional methods.

The following terms as used herein have the following meaning, unless otherwise specified.

The term "alkyl" as used herein, individually or in combination with other groups, refers to a straight or branched alkyl group containing 1-18 carbon atoms, including 1-12 carbon atoms, 1-8 carbon atoms and 1-6 carbon atoms. Reference to a single alkyl such as "n-propyl" specifically means a straight alkyl group, while reference to a single branched alkyl such as "isopropyl" specifically means a branched alkyl group. For example, "$C_{1-6}$alkyl" includes $C_{1-4}$alkyl, $C_{1-3}$alkyl, methyl, ethyl, n-propyl, isopropyl and tert-butyl. A similar meaning also applies to other groups as used throughout the present specification.

The term "alkoxyl" as used herein, refers to an alkyl group as defined above which is attached to a group "—O—", wherein the alkyl group contains 1-18 carbon atoms, including 1-12 carbon atoms, 1-8 carbon atoms, and methoxy, ethoxy and propoxyl.

The term "halogen" as used herein includes fluorine, chlorine, bromine and iodine.

The term "benzyl" as used herein refers to —$CH_2$-Ph group. When a benzyl is defined as "optionally substituted", it means that the benzyl can be in the form of an unsubstituted benzyl or a benzyl substituted with one or more suitable substituents at any appropriate position(s). Suitable substituents include, but are not limited to, halogen, hydroxyl, sulfhydryl, cyano, nitro, alkyl, aryl, alkoxy, heterocyclyl, haloalkyl, amino, alkylamino, amido, carboxyl, etc., as long as the resulting compounds have the properties as contemplated by the present disclosure. In one embodiment, the benzyl group is optionally substituted with one or more substituents selected from the group consisting of halogen, hydroxyl, sulfhydryl, cyano, nitro and amino.

The term "heterocyclyl" as used herein refers to a mono- or a fused ring system of 3-14, including 3-10, and 3-6 ring members, and contains one or more heteroatoms selected from nitrogen, oxygen, and sulfur.

The term "aryl" as used herein refers to an aromatic group containing 4-20 atoms, including 5-10 carbon atoms, the electrons of which follow the 4n+2 rule.

The term "classifying and counting" as used herein refers to classifying leukocytes into four groups by their differences in fluorescence and scattered light, wherein three groups correspond respectively to monocytes, lymphocytes and eosinophils and one group corresponds to neutrophils and basophils, and then counting the number of cells in each group.

The Reagent for Classifying and Counting Leukocytes

In one aspect, the present disclosure provides a reagent for classifying the leukocytes of a blood sample into at least four groups and then counting them. The four groups mean classifying leukocytes into four groups, wherein three groups respectively correspond to monocytes, lymphocytes and eosinophils and one group corresponds to neutrophils and basophils.

According to one aspect of the disclosure, the reagent for classifying and counting leukocytes comprises:
(1) a cyanine fluorescent dye; and
(2) a glycoside compound.

The Cyanine Fluorescent Dye.

The reagent disclosed herein comprises a fluorescent dye which specifically binds with nucleic acids in a cell (including DNA, RNA and organelles of similar nature) and is excited to emit fluorescence upon exposure to a laser with a certain wavelength.

In one embodiment, the fluorescent dye is a cyanine fluorescent dye. In another embodiment, the cyanine fluorescent dye is a compound having the general formula (I) or (II) or a combination thereof:

formula (I)

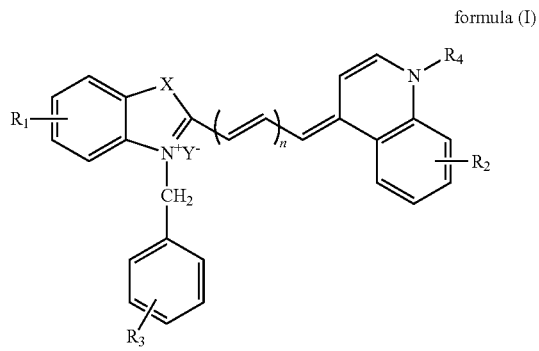

wherein
n is 1, 2 or 3;
X is $C(CH_3)_2$, O, S or Se;
$R_1$ and $R_2$ are each independently selected from H, $C_{1-18}$alkyl, $C_{1-6}$alkyl-$OR_5$ and halogen;
$R_3$ is H, $C_{1-18}$alkyl, $OR_5$, $C_{1-6}$alkyl-$OR_5$, $COOR_5$, $NO_2$, CN or halogen;
$R_4$ is $C_{1-18}$alkyl, $C_{1-6}$alkyl-$OR_5$, benzyl or halogen, wherein said benzyl is optionally substituted with one or more substituents independently selected from the group consisting of halogen, hydroxyl, sulfhydryl, cyano, nitro, alkyl, aryl, alkoxy, heterocyclyl, haloalkyl, amino, alkylamino, amido, and carboxyl;
$R_5$ is H or $C_{1-18}$alkyl; and
$Y^-$ is an anion;
In one embodiment, n is 1 or 2, and in another n is 1.
In one embodiment, X is $C(CH_3)_2$, O or S; or alternatively, X is $C(CH_3)_2$ or S; or X is S.
In one embodiment, $R_1$ and $R_2$ are each independently selected from at least one of the following: H, $C_{1-18}$alkyl and halogen; alternatively, $R_1$ and $R_2$ are each independently selected from at least one of the following: H and $C_{1-18}$alkyl; alternatively, $R_1$ and $R_2$ are each independently selected from at least one of the following: H and $C_{1-12}$alkyl; alternatively, $R_1$ and $R_2$ are each independently selected from at least one of the following: H and $C_{1-6}$alkyl; and in yet another embodiment $R_1$ and $R_2$ are both H.
In one embodiment, $R_3$ is H, $C_{1-18}$alkyl, $OR_5$, $COOR_5$, or halogen; alternatively, $R_3$ is H, $C_{1-12}$alkyl, $OR_5$, $COOR_5$, or halogen; alternatively, $R_3$ is H, $C_{1-6}$alkyl, $OR_5$, $COOR_5$, or halogen.
In one embodiment, $R_4$ is $C_{1-18}$alkyl, benzyl or halogen, wherein said benzyl is optionally substituted with one or more substituents independently selected from the group consisting of halogen, hydroxyl, sulfhydryl, cyano, nitro, alkyl, aryl, alkoxy, heterocyclyl, haloalkyl, amino, alkylamino, amido, and carboxyl; alternatively, $R_4$ is $C_{1-18}$alkyl, or benzyl, wherein said benzyl is optionally substituted with one or more substituents independently selected from the group consisting of halogen, hydroxyl, sulfhydryl, cyano, nitro, and amino; alternatively, $R_4$ is $C_{1-12}$alkyl, or benzyl, wherein said benzyl is optionally substituted with one or more substituents independently selected from the group consisting of halogen, hydroxyl, sulfhydryl, cyano, nitro, and amino; alternatively, $R_4$ is $C_{1-12}$alkyl, or benzyl, wherein said benzyl is optionally substituted with one or more substituents independently selected from the group consisting of halogen, hydroxyl, sulfhydryl, cyano, nitro, and amino; alternatively, $R_4$ is $C_{1-6}$alkyl, or benzyl, wherein said benzyl is optionally substituted with one or more substituents independently selected from the group consisting of halogen, hydroxyl, sulfhydryl, cyano, nitro, and amino.

In one embodiment, $R_5$ is H or $C_{1-12}$alkyl; alternatively, $R_5$ is H or $C_{1-6}$alkyl.

In one embodiment, $Y^-$ represents halogen ions, $ClO_4^-$, $PF_6^-$, $CF_3SO_3^-$, $BF_4^-$, acetate or p-toluenesulfonate anions.

In one embodiment, the cyanine fluorescent dye having the general formula (I) is selected from the following: compound A, compound B, and compound C.

Compound A

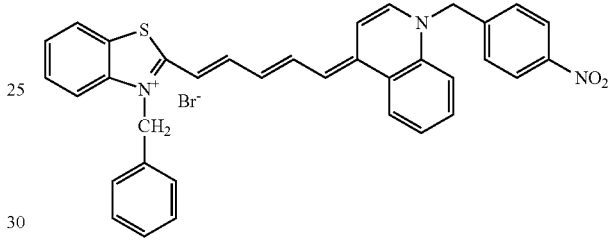

Compound B

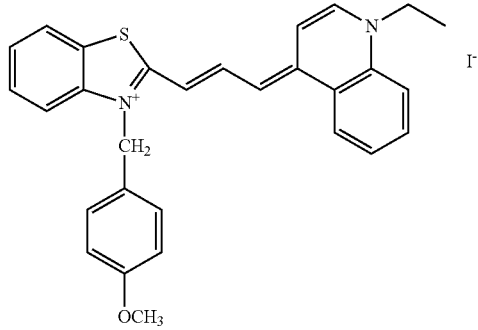

Compound C

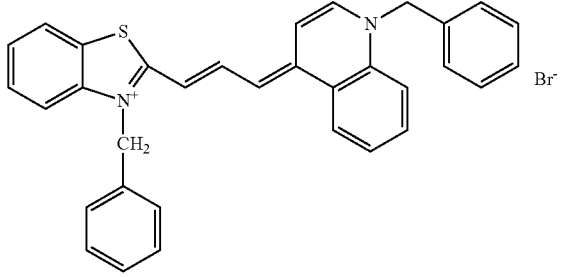

Reference is made to Chinese Patent Application No. 200710137258.6 for the compounds of formula (I) and the preparation thereof. Said Chinese Patent Application describes the synthesis of the compounds of formula (I) in detail, the disclosure of which is fully incorporated herein by reference.

formula (II)

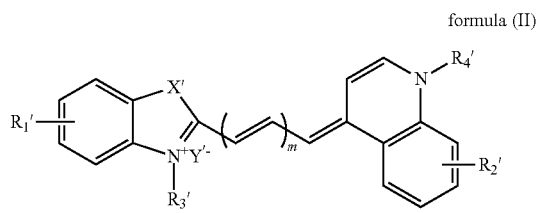

wherein m is 1, 2 or 3;

X' is C(CH$_3$)$_2$, O, S or Se;

R$_1$' and R$_2$' are each independently selected from H, OH, C$_{1-18}$alkyl, C$_{1-6}$alkyl-OR$_5$', C$_{1-18}$alkylsulfonate, phenyl and halogen;

R$_3$' and R$_4$' are each independently selected from C$_{1-18}$alkylCOOR$_6$', C$_{1-18}$alkylOR$_6$' and benzyl, wherein said benzyl is optionally substituted with one or more substituents independently selected from the group consisting of halogen, hydroxyl, sulfhydryl, cyano, nitro, alkyl, aryl, alkoxy, heterocyclyl, haloalkyl, amino, alkylamino, amido, and carboxyl, provided that R$_3$' and R$_4$' are not simultaneously benzyl, and R$_4$' is not C$_{1-18}$alkylOR$_6$' when R$_3$' is benzyl.

R$_5$' is H or C$_{1-18}$alkyl;

R$_6$' is H, phenyl or C$_{1-18}$alkyl, wherein said phenyl is optionally substituted with one or more substituents independently selected from the group consisting of halogen, hydroxyl, sulfhydryl, cyano, nitro, alkyl, aryl, alkoxy, heterocyclyl, haloalkyl, amino, alkylamino, amido, and carboxyl; and Y'$^-$ is an anion.

In one embodiment, m is 1 or 2; alternatively, m is 1.

In one embodiment, X' is C(CH$_3$)$_2$, O, or S; alternatively, X' is C(CH$_3$)$_2$, or S; alternatively, X' is S.

In one embodiment, R$_1$' and R$_2$' are each independently selected from H and C$_{1-18}$alkyl; alternatively, R$_1$' and R$_2$' are each independently selected from H and C$_{1-6}$alkyl; alternatively, R$_1$' and R$_2$' are both H.

In one embodiment, R$_3$' and R$_4$' are each independently selected from C$_{1-18}$alkylCOOR$_6$', C$_{1-18}$alkylOR$_6$' and benzyl, wherein said benzyl is optionally substituted with one or more substituents independently selected from the group consisting of halogen, hydroxyl, sulfhydryl, cyano, nitro, and amino; alternatively, R$_3$' and R$_4$' are each independently selected from C$_{1-6}$alkylCOOR$_6$', C$_{1-6}$alkylOR$_6$' and benzyl, wherein said benzyl is optionally substituted with one or more substituents independently selected from the group consisting of halogen, hydroxyl, sulfhydryl, cyano, nitro, and amino.

In one embodiment, R$_5$' is H or C$_{1-12}$alkyl; alternatively, R$_5$' is H or C$_{1-6}$alkyl.

In one embodiment, R$_6$' is phenyl or C$_{1-6}$alkyl, wherein said phenyl is optionally substituted with one or more substituents independently selected from the group consisting of halogen, hydroxyl, sulfhydryl, cyano, nitro, alkyl, aryl, alkoxy, heterocyclyl, haloalkyl, amino, alkylamino, amido, and carboxyl.

In one embodiment, Y$^-$ represents an anion, which can be any suitable anion, including but not limited to inorganic anions and organic anions, such as halogen ions, ClO$_4^-$, PF$_6^-$, CF$_3$SO$_3^-$, BF$_4^-$, acetate and p-toluenesulfonate anions.

In one embodiment, the cyanine fluorescent dye having the general formula (II) is selected from the following: compound D, compound E and compound F:

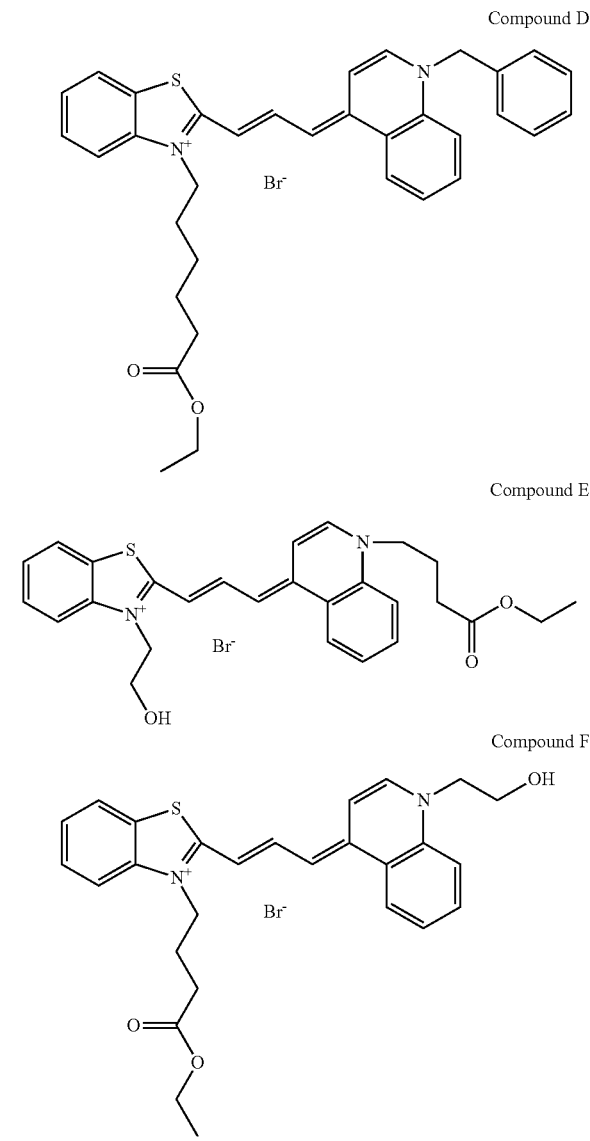

Reference is made to Chinese Patent Application No. 200810002503.7 for the compounds of formula (II) and the preparation thereof, the disclosure of which is fully incorporated herein by reference.

The cyanine fluorescent dye compound can be used directly for staining biological samples in the form of a salt as disclosed herein. Alternatively, in one embodiment of the present disclosure, the compounds of formula I and II can be used as a derivative thereof, which comprise, but is not limited to, conjugates.

Typically, conjugates are used in a fluorescence activated cell sorter (FACS). The term "conjugates" as used herein refers to the compounds formed by attaching the fluorescent dyes of the present disclosure to other molecules via covalent bonds. Molecules that can be conjugated with the fluorescent dyes of the present disclosure may be those that specifically bind to cells or cell components, including, but not limited to, antibodies, antigens, receptors, ligands, enzymes, substrates, and coenzymes.

The above cyanine fluorescent dye compound is used in some embodiments of the present disclosure in an appropriate concentration ranging from 0.002 ppm to 2000 ppm, including from 0.02 ppm to 200 ppm, and from 0.2 ppm to 20 ppm.

The cyanine fluorescent dye compound is stable in non-aqueous solvents, and thus may be preserved separately from the water soluble components of the reagent for classifying and counting leukocytes according to the present disclosure. The term "water soluble components" as used herein refers to the components of the present reagent for classifying and counting leukocytes such as the glycoside compound, the nonionic surfactant, and the anionic compound.

The Glycoside Compound.

The reagent for classifying and counting leukocytes further comprises a glycoside compound capable of rapidly lysing erythrocytes and subtly changing the leukocytes.

Said glycoside compound is a glycosidic nonionic surfactant. Typical glycoside compounds include alkyl glycosides and saponins.

An alkyl glycoside is a novel nonionic surfactant formed by dehydration between the hemi-acetal hydroxyl of a saccharide and the hydroxyl of an alcohol. The alkyl glycoside may be a single glycoside composed of certain alkyl groups and a certain saccharide, such as octyl glucoside, decyl glucoside, and lauryl maltoside. It also may be a mixture of multiple glycosides composed of different alkyl groups and different saccharides, such as the mixture of alkylglycosides prepared from $C_{8-10}$ natural aliphatic alcohols and glucose.

The glycoside compound useful in the reagent for classifying and counting leukocytes is represented by the following formula:

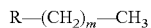

wherein m is an integer from 5 to 17, including from 6 to 14, and from 7 to 11; and R is a monosaccharide, a polymer of monosaccharides or a polysaccharide. More specifically, R is selected from common saccharides such as glucose, rhamnose, galactose, arabinose, xylose, maltose, mannose, ribose, lyxose, and fucose, deoxidated derivatives thereof, and polymers of these substances.

Saponins are complex glycosides widely found in many plants such as *Panax ginseng, Panax notoginseng, Anemarrhena asphodeloides, Palygala tenuifolia, Ural licorice, Platycodon grandiflorum,* and *Chinese bupleurum.* Saponins are composed of a sapogenin in combination with a saccharide, an alduronic acid or another organic acid. Typical saccharides include D-glucose, L-rhamnose, D-galactose, L-arabinose, or L-xylose. Typical alduronic acids include glucuronic acid and galacturonic acid. Saponins can be divided into two kinds according to their sapogenin component; the steroidal saponins and the triterpenoid saponins. Steroidal saponins comprise a derivative of spirostane as the sapogenin, usually contain twenty seven (27) carbon atoms (such as dioscin) and are usually found in Liliaceae and Dioscoreaceae spp. Triterpenoid saponins comprise a derivative of triterpene as the sapogenin, and usually contain thirty (30) carbon atoms. Triterpenoid saponins are further classified into tetracyclic triterpenoids and pentacyclic triterpenoids, and usually are found in Araliaceae and Umbelliferae spp.

Steroidal saponins useful for classifying and counting leukocytes according to the present disclosure usually have the structure as shown by formula A or B:

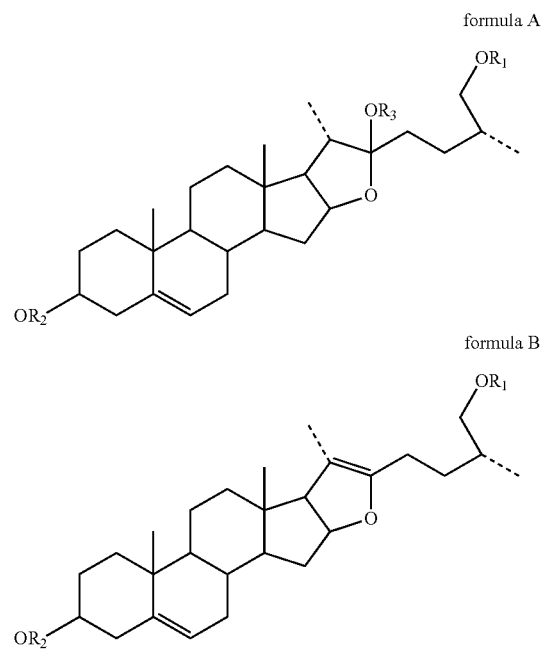

wherein $R_3$ is H or $CH_3$;

$R_1$ is a common saccharide such as glucose, rhamnose, galactose, arabinose, xylose, maltose, mannose, ribose, lyxose, and fucose, or deoxidated derivatives thereof; and $R_2$ is a straight-chain or branched-chain saccharide, with its compositional monosaccharide selected from common saccharides such as glucose, rhamnose, galactose, arabinose, xylose, maltose, mannose, ribose, lyxose, and fucose, and deoxidated derivatives thereof.

Trierpenoid saponins useful for classifying and counting leukocytes according to the present disclosure usually have the following structure:

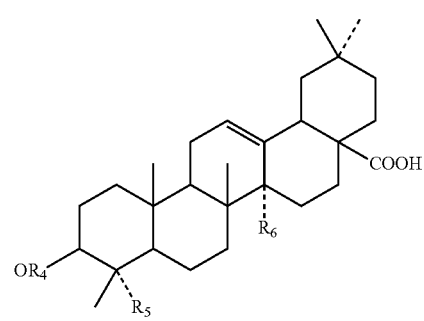

wherein $R_4$ is a straight-chain or branched-chain saccharide, with its compositional monosaccharide selected from common saccharides such as glucose, rhamnose, galactose, arabinose, xylose, maltose, mannose, ribose, lyxose, and fucose, and deoxidated derivatives thereof;

$R_5$ is $CH_3$ or $CH_2OH$; and
$R_6$ is $CH_3$ or $CH_2OH$;

or

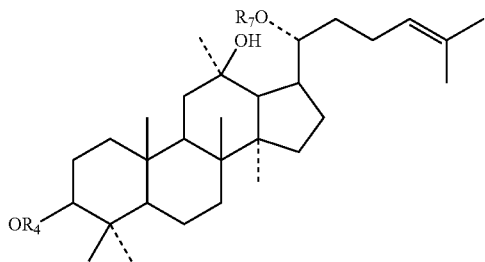

wherein
$R_4$ and $R_7$ are, independently of one another, a straight-chain or branched-chain saccharide, with its compositional monosaccharide selected from common saccharides such as glucose, rhamnose, galactose, arabinose, xylose, maltose, mannose, ribose, lyxose, and fucose, and deoxidated derivatives thereof;

or

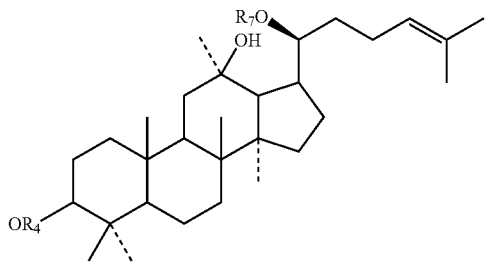

wherein
$R_4$ and $R_7$ are, independently of one another, a straight-chain or branched-chain saccharide, with its compositional monosaccharide selected from common saccharides such as glucose, rhamnose, galactose, arabinose, xylose, maltose, mannose, ribose, lyxose, and fucose, and deoxidated derivatives thereof;

or

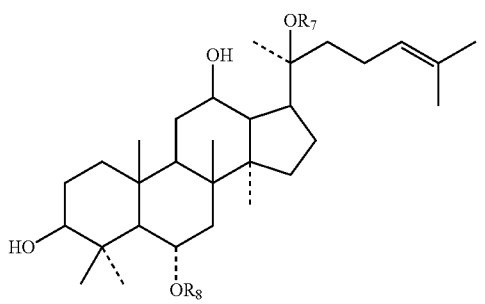

wherein
$R_7$ and $R_8$ are, independently of one another, a straight-chain or branched-chain saccharide, with its compositional monosaccharide selected from common saccharides such as glucose, rhamnose, galactose, arabinose, xylose, maltose, mannose, ribose, lyxose, and fucose, and deoxidated derivatives thereof.

Compared with conventional surfactants, a glycosidic nonionic surfactant provides the following advantages: it is readily available from a wide variety of sources; it is non-toxic, non-irritative, and mild to the human skin; it is rapidly and completely biodegradable, and it is available from renewable resources.

In addition, as a nonionic surfactant with hemolytic activity, the glycosidic surfactant is capable of lysing erythrocytes at a lower concentration. After the lysis of erythrocytes, the glycosidic surfactant is also capable of reducing the size of erythrocyte fragments and preventing the aggregation of ghost cells. The glycosidic surfactant is also able to damage the membrane of erythrocytes which are normally resistant to surfactants, to ensure a correct analysis of leukocytes.

At the same time, the presence of the glycosidic surfactant allows for some damage to the leukocytes when lysing erythrocytes. Some of the compositional components of the membrane of leukocytes (which may be some lipid molecules) may be damaged by the glycosidic surfactant, and pores may arise in the leukocyte membrane. The pores connect the inside of the cell with the outside, so that the intracellular materials may flow out while the extracellular materials may enter. As a result, fluorescent dye markers may enter the cell rapidly to bind the intracellular nucleic acids (DNA or RNA).

Saponins are generally a mixture of natural extracts, and are a complex mixture of different combinations of saccharides with terpenoid or steroid moieties, which may result in differential treatment levels and thus poor uniformity of the treated cells, looseness of each subpopulation of cells, poor repeatability and poor production feasibility.

In contrast, alkyl glycosides may be in the form of a single compound, and thus may have the advantages of a better uniformity of the treatment, a better aggregation level for each subpopulation of cells, as well as a better production feasibility. Therefore, alkyl glycosides are preferably used in the reagent for classifying and counting leukocytes according to the present disclosure.

The amount of the aforementioned glycosidic surfactant depends upon the property of chosen glycoside, reaction time, reaction temperature, and the amount of other components, and generally ranges from 0.025 g/L to 10 g/L, including from 0.05 g/L to 0.5 g/L.

The Nonionic Surfactant.

Optionally, the present reagent for classifying and counting leukocytes may further comprise a nonionic surfactant other than glycoside compounds. It is used for the pyknosis of intracellular materials, amplifying the intensity difference of scattered light from the intracellular structures of different leukocyte subpopulation, and protecting leukocytes from excessive damage.

The nonionic surfactant may be selected from those represented by formula (III):

$$R_1\text{—}R_2\text{—}(CH_2CH_2O)_n\text{—}H \qquad \text{formula (III)}$$

wherein
$R_1$ is a $C_{8\text{-}23}$alkyl or $C_{8\text{-}23}$alkenyl, and includes a straight-chain alkyl selected from octyl, decyl, lauryl, myristyl, cetyl and stearyl. In some embodiments, it is a straight-chain alkyl selected from lauryl, myristyl and cetyl;
$R_2$ is —O—,

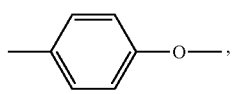

or —COO—; and
n is an integer from 10 to 30.

Nonionic surfactants of polyoxyethylene type having the general formula (III) and a HLB value of from 10 to 20 are suitable for the present disclosure. In some embodiments, it includes those such as polyoxyethylene (15) cetyl ether, polyoxyethylene (21) lauryl ether, polyoxyethylene (23) cetyl ether, polyoxyethylene (25) cetyl ether, polyoxyethylene (30) cetyl ether and the like.

The concentration of the aforementioned nonionic surfactant of polyoxyethylene type depends upon the specific surfactant used. The concentration may be from 0.05 g/L to 1.5 g/L, including from 0.1 g/L to 1.0 g/L for polyoxyethylene (21) lauryl ether; from 0.05 g/L to 1.5 g/L, including from 0.1 g/L to 1.0 g/L for polyoxyethylene (23) cetyl ether; from 0.05 g/L to 1.5 g/L, including from 0.1 g/L to 1.0 g/L for polyoxyethylene (25) cetyl ether; and from 0.03 g/L to 1.0 g/L, including from 0.05 g/L to 0.8 g/L for polyoxyethylene (30) cetyl ether.

Without being bound by theory, and although the reaction mechanism of nonionic surfactants is still unclear, it is believed that they are capable of binding to the membrane of leukocytes and thus protecting the membrane from lysis by hemolytic agents. In some cases, for example, the addition of a nonionic surfactant is desirable when the hemolytic activity of the glycosidic compound is strong. In addition, a nonionic surfactant is also capable of subjecting the cells to appropriate shrinkage and solidification, and thus amplifying the intensity difference of scattered light from the intracellular structures of different leukocyte subpopulation.

The nonionic surfactant contained in the reagent for classifying and counting leukocytes according to the present disclosure may be one nonionic surfactant or a combination of two or more nonionic surfactants. For the combination of two or more nonionic surfactants, the aforementioned concentration for a single nonionic surfactant is used for each nonionic surfactant, and is optimized for the overall effect.

The Anionic Compound Carrying One or More Carboxyl or Sulfonate Groups.

Optionally, the reagent of the present disclosure may further comprise an anionic organic compound capable of providing morphological differentiation to the leukocytes. The anionic organic compound may bind to charged cationic components of a damaged cell, and thus can change the complexity of content for different subpopulations of cells. Especially after the shrinkage of cells, the morphological change will be significantly amplified to increase the scattered light intensity differences of different cells, and thus facilitate their differentiation. On the other hand, the anionic organic compound may also bind to the fluorescent dye to decrease the fluorescence intensity of the cells, which makes the fluorescence intensity more uniform for each subpopulation of cells, and the fluorescence distribution of each subpopulation will be less loose and more concentrated in the scattergram.

The anionic organic compound may be selected from an acid carrying one or more carboxyl or sulfonate groups and salts thereof.

In one embodiment, the carboxylic acid carrying one carboxyl group and salts thereof is selected from formic acid and alkali metal salts thereof, acetic acid and alkali metal salts thereof, and benzoic acid and alkali metal salts thereof. In a further embodiment, the carboxylic acid carrying more than one carboxyl groups and salts thereof is selected from citric acid and alkali metal salts thereof, malic acid and alkali metal salts thereof, and phthalic acid and alkali metal salts thereof.

The anionic compound may also be a sulfonic acid carrying one or more sulfonate groups and salts thereof, and includes those such as benzene sulfonic acid and alkali metal salts thereof, α-naphthalene sulfonic acid and alkali metal salts thereof, taurine and alkali metal salts thereof, and sulfobenzene sulfonic acid and alkali metal salts thereof.

There is no limitation to the concentration of the aforementioned anionic compound as long as a better classification of leukocytes can be achieved. It may be in the range from 0.05 g/L to 25 g/L, including from 0.5 g/L to 5 g/L. It is also possible to adjust the concentration according to the kind of compounds used.

The Alcohol.

The reagent of the present disclosure may also comprise an amount of alcohol. Without being bound to any theory, it is believed that the alcohols may solidify the cells, improve their membrane permeability, and thus facilitate the fluorescent dye in penetrating the membrane and lower the concentration of dye which is used. In addition, the alcohol may also help in the treatment of cells with an exceptionally lysis-tolerant membrane. That is, the alcohol may have a solubilization effect, improving the treatment of the exceptional cells. There is no special requirement regarding the type of alcohols, and it is appropriate to use common alcohols such as methanol, ethanol, ethylene glycol, isopropanol, and 2-phenoxyl ethanol for the present disclosure.

The concentration of the aforementioned alcohol depends upon the kind of alcohol used. For example, in certain embodiments, the concentration is from 30 g/L to 150 g/L for methanol, from 20 g/L to 100 g/L for ethanol, and from 0.5 g/L to 5 g/L for 2-phenoxyl ethanol. Generally speaking, the concentration of an alcohol decreases with the increase of the number of carbon atoms of the alcohol.

The Additional Additives.

The present reagent may also comprise a buffering agent for maintaining the pH of the reagent from about 5 to about 10. There is no special requirement regarding the type of buffering agent, and it is appropriate to use common buffering systems such as phosphate buffer, borate buffer, Tris, and HEPES for the present disclosure. The buffering agent is usually used in an amount of between about 10 to about 500 mM.

The reagent of the present disclosure may also comprise other conventional additives such as preservatives and metal chelating agents for the preservation and long-term storage of the reagent. There is no special requirement regarding the type of preservative, and it is appropriate to use preservatives commonly available in the market such as kathon and gentamicin, and metal chelating agents such as EDTA and its alkali metal salts for the present disclosure. These additives are generally used at a concentration which does not affect the classification and counting of the leukocytes.

The osmolarity of the reagent of the present disclosure is generally between 10 mOsm to 100 mOsm. Such an osmolarity is helpful for lysing erythrocytes and platelets, and thus enables the use of a lower amount of hemolytic agent.

The Reagent Kit for Classifying and Counting Leukocytes

In another aspect, the present disclosure relates to a reagent kit for classifying and counting leukocytes, wherein the kit comprises the reagent for classifying and counting leukocytes according to the present disclosure. The kit may be used to treat blood samples and classify and count the leukocytes in the samples into four subpopulations.

In the kit, all components of the reagent can be provided in the form of a single package, or alternatively in the form of two or more separate packages, with the cyanine fluorescent dye packaged separately from the other components.

The cyanine fluorescent dye compound used in the present reagent is stable in non-aqueous solvents, and thus may be preserved separately from the water soluble components of the present reagent. The cyanine fluorescent dye may also be preserved in organic solvents. There is no special requirement regarding to the organic solvent, as long as it can sufficiently dissolve the cyanine fluorescent dye and has certain water solubility. Common organic solvents are suitable to use in the present disclosure include methanol, ethanol, ethylene glycol, glycerol, and dimethyl sulfoxide.

The cyanine fluorescent dye may be preserved in an organic solvent at a concentration which is over the final working concentration and ensures the sufficient dissolution of the dye. The cyanine fluorescent dye is generally preserved in an organic solvent at a concentration from 0.01 ppm to 1000 ppm, including from 1 ppm to 100 ppm.

In the present disclosure, the water soluble components are also referred to as a "hemolytic agent", and the components comprising the cyanine fluorescent dye are also referred to as a "staining solution". When the present kit is used, the staining solution, the blood sample and the hemolytic agent are mixed at a certain volume ratio for a period of time before performing the assay, or the staining solution may be first mixed with the hemolytic agent and then the resultant mixture is mixed with the blood sample at a certain volume ratio. There is no special requirement regarding to the ratio between the staining solution and the hemolytic agent, and it is generally suitable to mix them at a ratio from 1:10 to 1:100, including from 1:40 to 1:60.

In another aspect, the present disclosure relates to a process for preparing a reagent kit for classifying and counting leukocytes, wherein the process comprises:

dissolving an amount of each component of the present reagent into water, adjusting the pH of the solution and diluting to a certain volume, and packaging it in the kit in the form of a single package; or dissolving an amount of cyanine fluorescent dye of the present reagent into an organic solvent, diluting to a certain volume and packaging; dissolving an amount of each of the other components of the present reagent into water, adjusting the pH of the solution and diluting to a certain volume, and packaging; packing the two separate packages in the form of a kit. The term "other components" as used herein refers to the water soluble components in the present reagent other than the cyanine fluorescent dye. It is possible to dissolve the other components into water together, then adjust the pH and dilute to a certain volume, and pack it in the kit in the form of a single package. It is also possible to dissolve each of the other components into water separately, then adjust the pH and dilute to a certain volume, and pack them in the kit in the form of multiple packages.

As mentioned above, the cyanine fluorescent dye compound used in the present reagent is stable in non-aqueous solvents. Thus, in an embodiment, the cyanine fluorescent dye is first preserved separately from the water soluble components of the present reagent. In a further embodiment, the cyanine fluorescent dye is preserved in an organic solvent. Then, the cyanine fluorescent dye is packed in the kit separately from the other components.

Process for Classifying and Counting Leukocytes

In still another aspect, the present disclosure relates to a process for classifying and counting leukocytes, wherein the process comprises the following steps:

(1) mixing a blood sample in the present reagent or in a kit comprising the present reagent for a period of time to lyse erythrocytes and platelets, and to damage leukocytes to provide morphological changes to each subpopulation of leukocyte, and then labeling the nucleic acids in the leukocytes with a fluorescent dye;

(2) classifying the leukocytes into at least four groups, three of which correspond to monocytes, lymphocytes and eosinophils and one group corresponding to neutrophils and basophils, and then counting the cell number in each group, by measuring any two of the following: the information on side-scattered light intensity, the information on forward-scattered light intensity, and the information on side fluorescence intensity. In an embodiment, the process comprises measuring the information on side-scattered light intensity and side fluorescence intensity.

The mixing step is carried out over a period of time from 5 to 30 seconds, including from 15 to 25 seconds. The present reagent interacts rapidly with the leukocyte to partly damage its membrane, so that the dye may enter the leukocyte rapidly to label the nucleic acids in the leukocyte. Therefore, it is possible to achieve a fast classification and count of leukocytes with the present process, which is favorable for accelerating the assays with automated instrumentation and especially suitable for the large-scale assaying of blood samples.

In the process of classification according to the present disclosure, there is no special requirement regarding to the ratio between the blood sample and the present reagent, and it is generally suitable to mix them at a ratio from 1:10 to 1:100, including from 1:40 to 1:60.

The temperature at which the classification takes place may be from 20° C. to 50° C., and includes from 35° C. to 45° C.

The fluorescence intensity information according to the present disclosure may be determined by measuring the side excitation fluorescence at 90° with a laser flow cytometry method. The information on intracellular morphological features may be determined by measuring the side-scattered light at 90° with a laser flow cytometry method. The information on cell size may be determined by measuring forward-scattered light at 1-5° with an impedance method or a laser flow cytometry method. The laser flow cytometry method may be carried out with known instruments such as the one shown in FIG. 1. The laser source may be a laser whose wavelength adapt to the excitation wavelength of the fluorescent dye used.

In one embodiment, the process according to the present disclosure comprises the following steps:

1. mixing a blood sample with the present reagent to lyse erythrocytes and platelets, and damage leukocytes to provide morphological and intracellular structural changes to each subpopulation of leukocyte, and labeling the nucleic acids in the leukocytes with a fluorescent dye to form a test sample suspension;

2. ensheathing the sample suspension with sheath fluid, arranging the samples in a single line and passing them sequentially through the optical detection area of the flow chamber, then collecting the information on scattered light intensity and side fluorescence intensity of the cells upon exposure to laser radiation;

3. analyzing the information on scattered light intensity and side fluorescence intensity, and classifying and counting the leukocytes by means of the differences of each subpopulation of leukocytes in their scattered light and fluorescence signal, in a two-dimensional or three-dimensional scattergram plotted by the scattered light intensity and side fluorescence intensity. Said information on scattered light intensity refers to the information on side-scattered light intensity, or the information on forward-scattered light intensity. Accordingly, the classification and counting may be carried out with a three-dimensional scattergram formed by the information on side-scattered light intensity, forward-scattered light intensity, and side fluorescence intensity, or a two-dimensional scattergram formed by any two of the information on side-scattered light intensity, the information on forward-scattered light intensity, and the information on side fluorescence intensity.

In an embodiment, the classification and counting of leukocytes according to the present disclosure is carried out with a two-dimensional scattergram formed by the information on side-scattered light intensity and side fluorescence intensity. In a further embodiment, it is carried out with a three-dimensional scattergram formed by the information on side-scattered light intensity, forward-scattered light intensity, and side fluorescence intensity.

The disclosure is further described with reference to the following non-limiting examples.

Unless otherwise indicated, the reagents used in the examples are above the grade of Chemical Pure. The instrument used to test blood cells is BC series of flow cytometer at 640 nm (SHENZHEN MINDRAY BIO-MEDICAL ELECTRONICS CO., LTD). The schematic diagram of the optical system of the cell analyzer is as shown in FIG. 1.

EXAMPLES

Example 1

| Fluorescent dye A | 0.5 ppm |
| Dodecyl glucoside | 0.05 g/L |
| Phosphate buffer | 20 mM |
| pH | 7.0 |

Phosphate buffer (20 mM) was prepared (pH 7.0). The indicated amount of fluorescent dye and dodecyl glucoside was added into 800 ml of phosphate buffer, and was mixed to dissolve. The solution was then diluted to the desired volume with phosphate buffer, filtered, and stored for future use.

Figure 2:
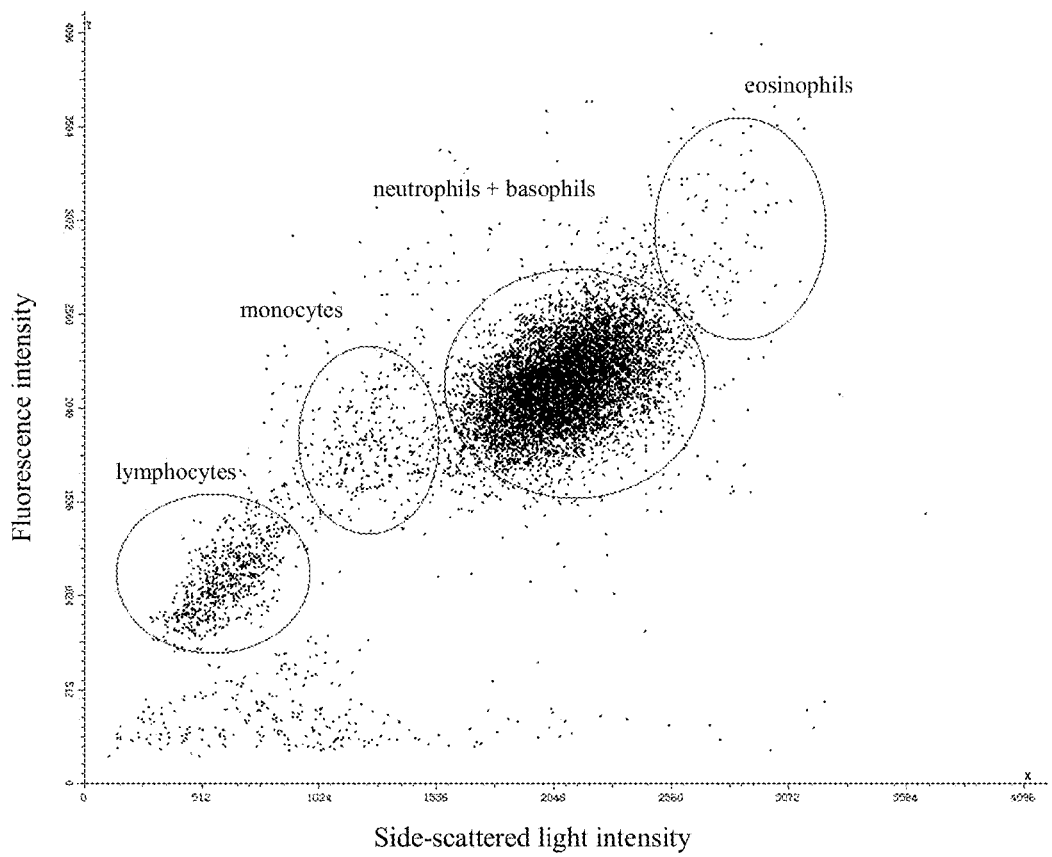
FIG. 2 is a scattergram showing the leukocyte classification obtained in Example 1 of the present specification, wherein the X-axis is the intensity of side-scattered light, and the Y-axis is the intensity of fluorescence.

20 μl of fresh anti-coagulation blood sample was added to 1 ml of the above reagent, mixed for 25 seconds while the temperature was kept at 35° C., then the leukocytes were detected according to a laser flow cytometry method (Laser source: Red semiconductor laser, Wavelength: 633 nm). The information on the fluorescence intensity of the cells was detected by side fluorescence at a detection angle of 90°, and the information on the side-scattered light intensity of the cells was detected by side-scattered light at a detection angle of 90°. As shown in FIG. 2, the leukocytes were classified into four groups corresponding to lymphocytes, monocytes, neutrophils, and eosinophils, respectively.

Example 2

| Fluorescent dye E | 0.5 ppm |
| Saponin | 0.05 g/L |
| Polyoxylene (15) cetyl ether | 0.8 g/L |
| Phosphate buffer | 20 mM |
| pH | 7.0 |

Figure 3:
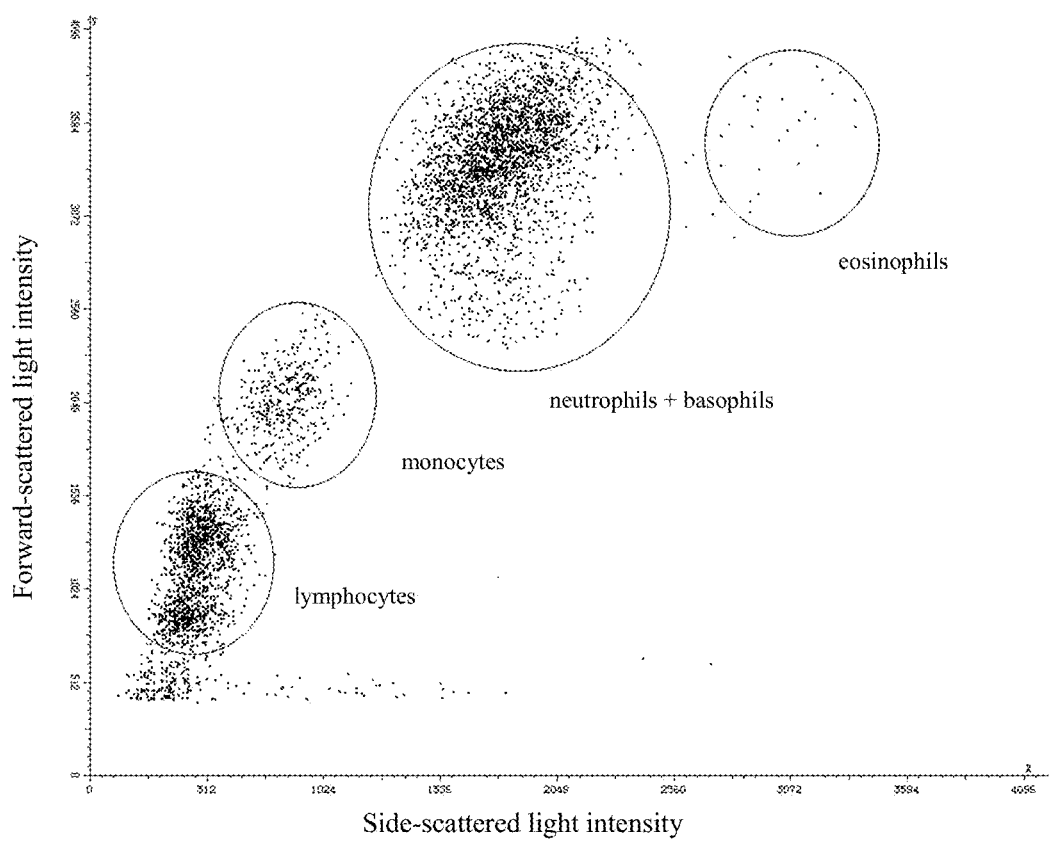
FIG. 3 is a scattergram showing the leukocyte classification obtained by the process disclosed in Example 2 of the present specification, wherein the X-axis is the intensity of side-scattered light, and the Y-axis is the intensity of forward-scattered light.

Following the procedure of Example 1, a reagent was prepared with the above ingredients. The saponin was supplied from Tokyo Chemical Industry Co., Ltd. 20 μl of fresh anti-coagulation blood sample was added to 1 ml of the above reagent, mixed for 23 seconds while the temperature was kept at 43° C., then leukocytes were detected according to a laser flow cytometry method (Laser source: Red semiconductor laser, Wavelength: 633 nm). The information on side-scattered light intensity of the cells was detected by side-scattered light at a detection angle of 90°, and the information on the forward-scattered light intensity of the cells was detected by low angle scattered light at 1° to 5°. As shown in FIG. 3, the leukocytes were classified into four groups corresponding to lymphocytes, monocytes, neutrophils, and eosinophils, respectively.

Example 3

| Fluorescent dye A | 0.5 ppm |
| Octyl glucoside | 0.1 g/L |
| Sodium salicylate | 2.0 g/L |
| HEPES | 20 mM |
| pH (adjust pH with NaOH) | 7.0 |

Figure 4:
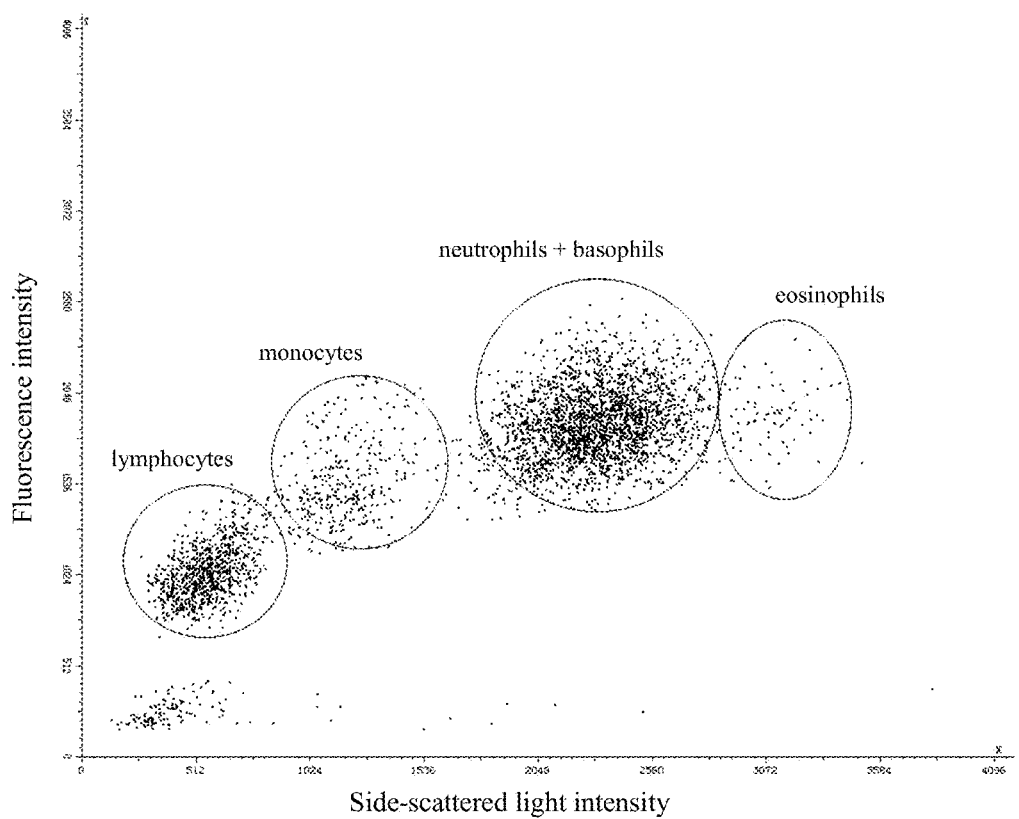
FIG. 4 is a scattergram showing the leukocyte classification obtained by the process disclosed in Example 3 of the present specification, wherein the X-axis is the intensity of side-scattered light, and the Y-axis is the intensity of fluorescence.

Following the procedure of Example 1, a reagent was prepared with the above ingredients. 20 μl of fresh anti-coagulation blood sample was added to 1 ml of the above reagent, mixed for 25 seconds while the temperature was kept at 38° C., then leukocytes were detected according to a laser flow cytometry method (Laser source: Red semiconductor laser, Wavelength: 633 nm). The information on the fluorescence intensity of the cells was detected by side fluorescence at 90°, and the information on the side-scattered light intensity of the cells was detected by side-scattered light at 90°. As shown in FIG. 4, the leukocytes were classified into four groups corresponding to lymphocytes, monocytes, neutrophils, and eosinophils, respectively.

Example 4

| Fluorescent dye C | 1.0 ppm |
| Saponin | 0.6 g/L |
| Tris | 40 mM |
| Sodium citrate | 5 g/L |
| Polyoxylene (23) cetyl ether | 0.5 g/L |
| pH (adjust pH with HCl) | 7.5 |

Figure 5:
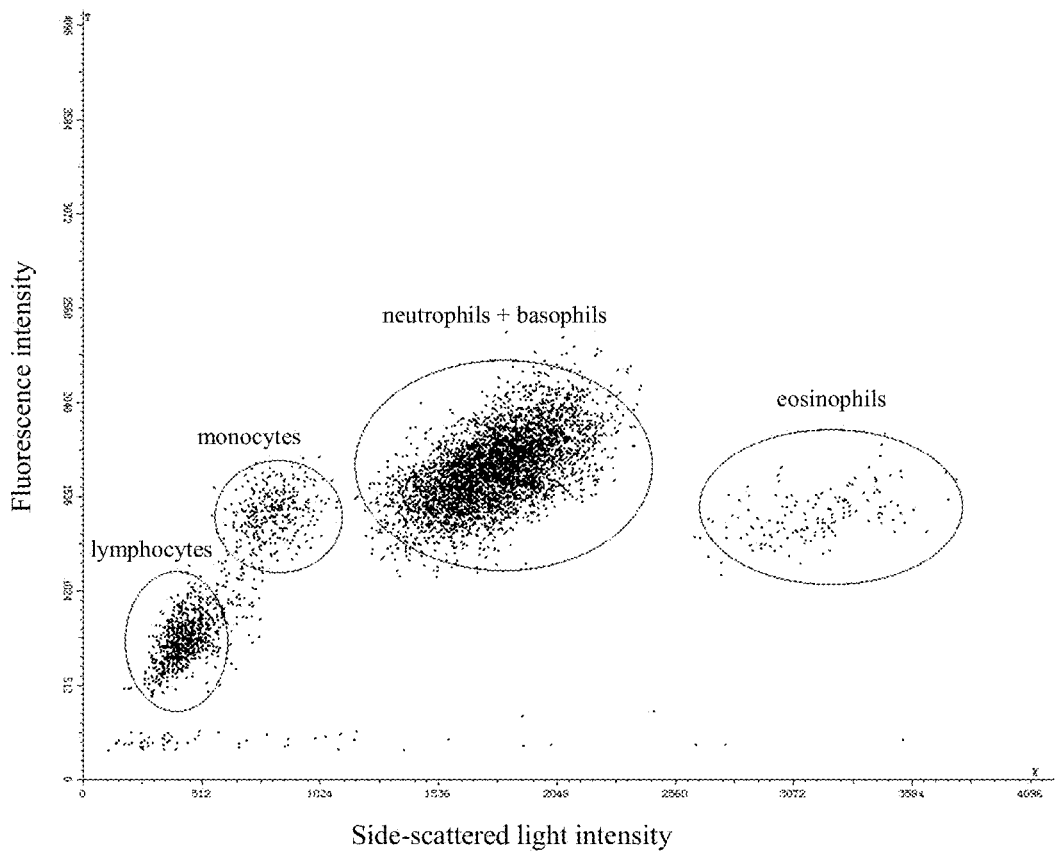
FIG. 5 is a scattergram showing the leukocyte classification obtained by the process disclosed in Example 4 of the present specification, wherein the X-axis is the intensity of side-scattered light, and the Y-axis is the intensity of fluorescence.

Following the procedure of Example 1, a reagent was prepared with the above ingredients. The saponin was supplied from Tokyo Chemical Industry Co., Ltd. 20 μl of fresh anti-coagulation blood sample was added to 1 ml of the above reagent, mixed for 23 seconds while the temperature was kept at 40° C., then leukocytes were detected according to a laser flow cytometry method (Laser source: Red semiconductor laser, Wavelength: 633 nm). The information on the fluorescence intensity of the cells was detected by side fluorescence at 90°, and the information on the side-scattered light intensity of the cells was detected by side-scattered light at 90°. As shown in FIG. 5, the leukocytes were classified into four groups corresponding to lymphocytes, monocytes, neutrophils, and eosinophils, respectively.

Example 5

| | |
|---|---|
| Fluorescent dye B | 1.0 ppm |
| Saponin | 0.6 g/L |
| Tris | 40 mM |
| Sodium citrate | 5 g/L |
| Polyoxylene (25) cetyl ether | 0.5 g/L |
| pH (adjust pH with HCl) | 7.5 |

Figure 6:
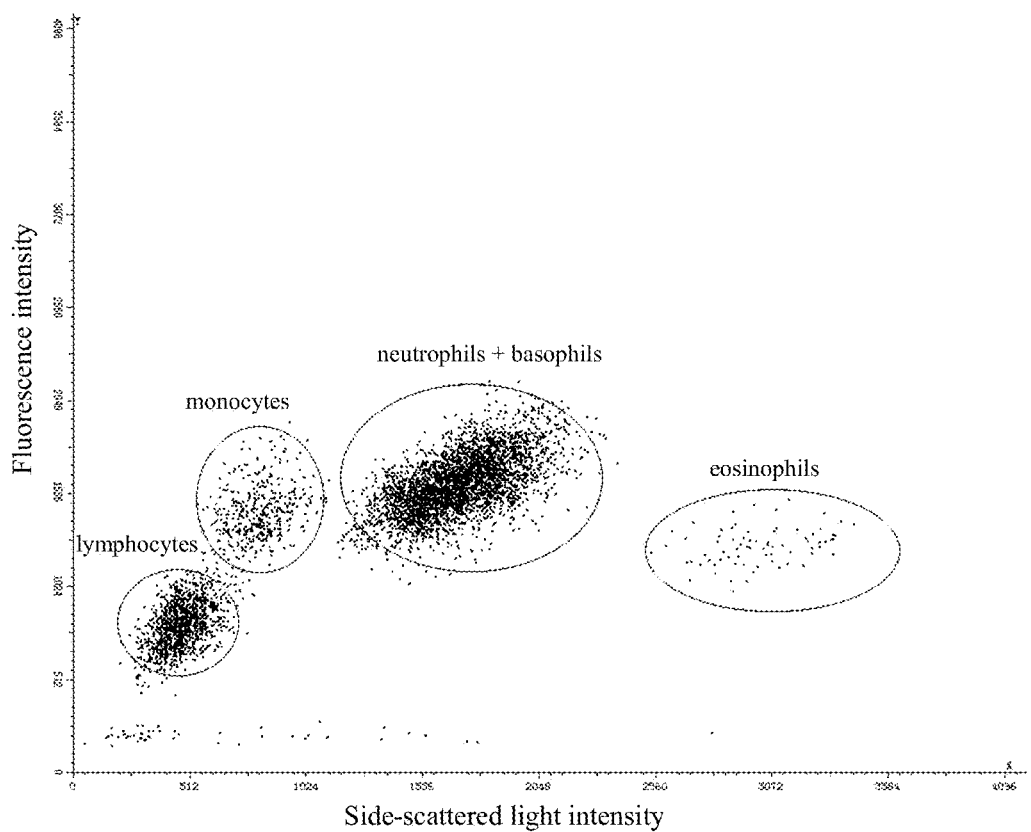
FIG. 6 is a scattergram showing the leukocyte classification obtained by the process disclosed in Example 5 of the present specification, wherein the X-axis is the intensity of side-scattered light, and the Y-axis is the intensity of fluorescence.

Following the procedure of Example 1, a reagent was prepared with the above ingredients. The saponin was supplied from Tokyo Chemical Industry Co., Ltd. 20 μl of fresh anti-coagulation blood sample was added to 1 ml of the above reagent, mixed for 23 seconds while the temperature was kept at 42° C., then leukocytes were detected according to a laser flow cytometry method (Laser source: Red semiconductor laser, Wavelength: 633 nm). The information on the fluorescence intensity of the cells was detected by side fluorescence at 90°, and the information on the side-scattered light intensity of the cells was detected by side-scattered light at 90°. As shown in FIG. 6, the leukocytes were classified into four groups corresponding to lymphocytes, monocytes, neutrophils, and eosinophils, respectively.

Example 6

| | |
|---|---|
| Fluorescent dye B | 1.0 ppm |
| Saponin | 0.6 g/L |
| Tris | 40 mM |
| Sodium citrate | 5 g/L |
| Ethylene glycol | 5 g/L |
| pH (adjust pH with HCl) | 7.5 |

Figure 7:
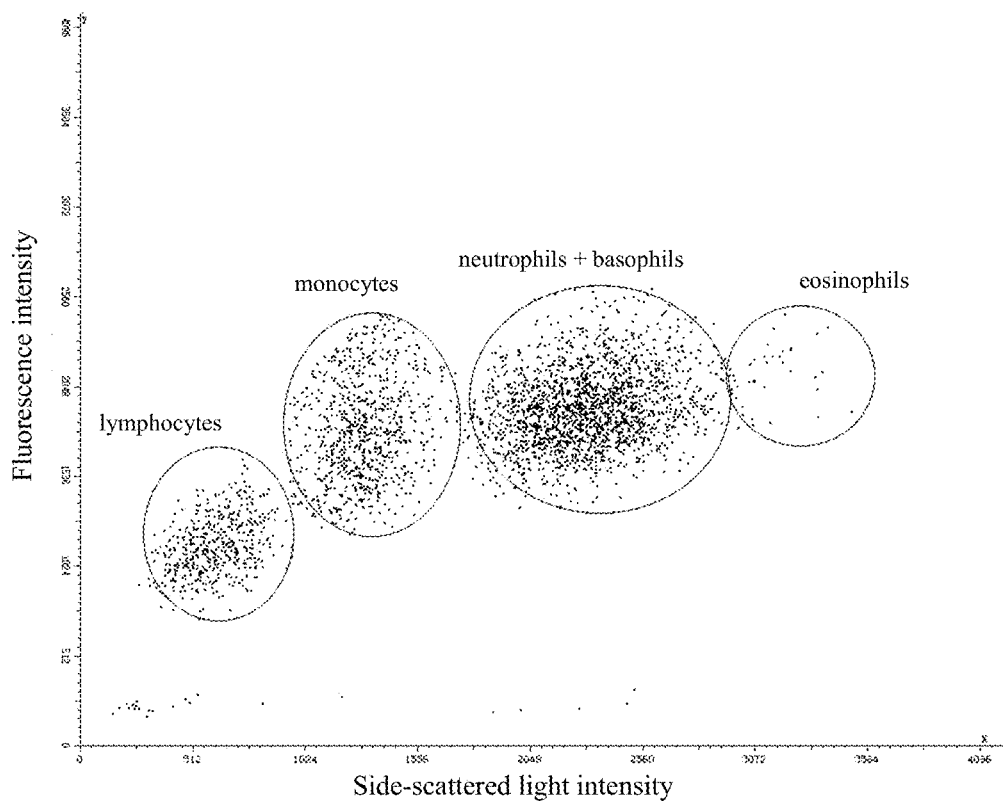
FIG. 7 is a scattergram showing the leukocyte classification obtained by the process disclosed in Example 6 of the present specification, wherein the X-axis is the intensity of side-scattered light, and the Y-axis is the intensity of fluorescence.

Following the procedure of Example 1, a reagent was prepared with the above ingredients. The saponin was supplied from Tokyo Chemical Industry Co., Ltd. 20 μl of fresh anti-coagulation blood sample was added to 1 ml of the above reagent, mixed for 23 seconds while the temperature was kept at 44° C., then leukocytes were detected according to a laser flow cytometry method (Laser source: Red semiconductor laser, Wavelength: 633 nm). The information on the fluorescence intensity of the cells was detected by side fluorescence at 90°, and the information on the side-scattered light intensity of the cells was detected by side-scattered light at 90°. As shown in FIG. 7, the leukocytes were classified into four groups corresponding to lymphocytes, monocytes, neutrophils, and eosinophils, respectively.

Example 7

| | |
|---|---|
| Fluorescent dye D | 2.0 ppm |
| Decyl maltoside | 0.1 g/L |
| HEPES | 20 mM |
| Polyoxylene (21) lauryl ether | 0.9 g/L |
| 2-phenoxyl ethanol | 1.0 g/L |
| pH (adjust pH with NaOH) | 7.2 |

Figure 8:
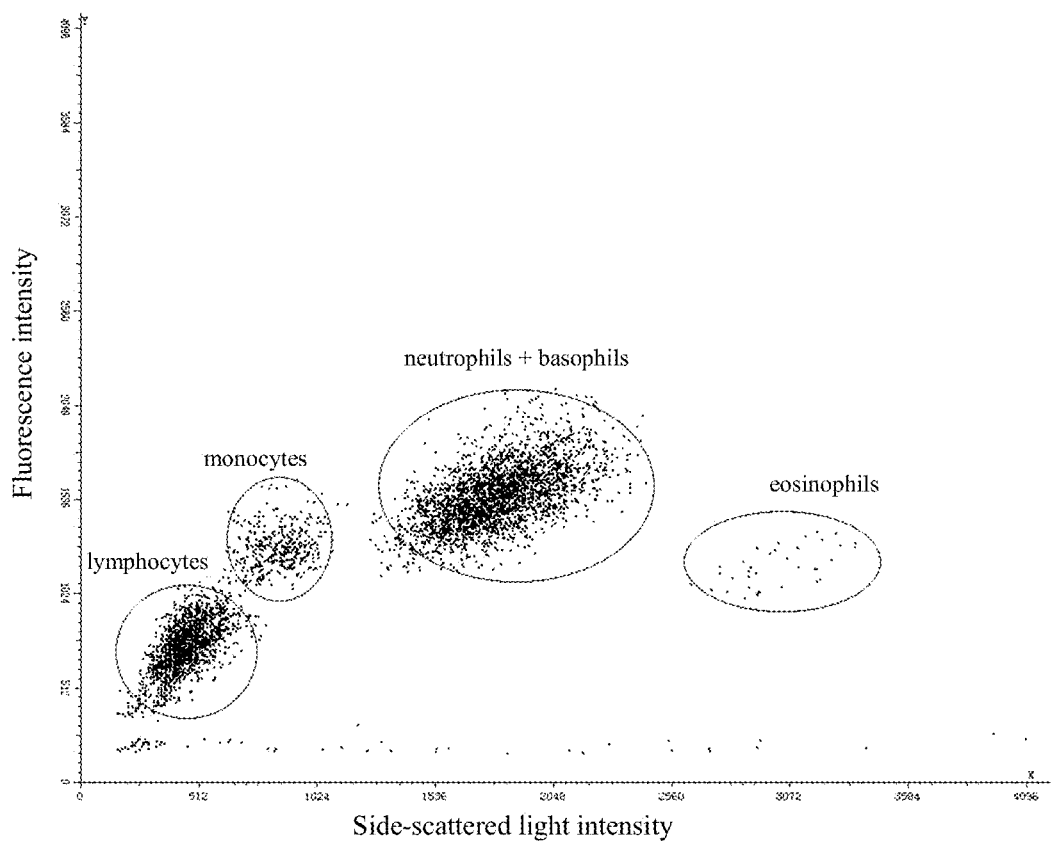
FIG. 8 is a scattergram showing the leukocyte classification obtained by the process disclosed in Example 7 of the present specification, wherein the X-axis is the intensity of side-scattered light, and the Y-axis is the intensity of fluorescence.

Following the procedure of Example 1, a reagent was prepared with the above ingredients. 20 μl of fresh anti-coagulation blood sample was added to 1 ml of the above reagent, mixed for 20 seconds while the temperature was kept at 42° C., then leukocytes were detected according to a laser flow cytometry method (Laser source: Red semiconductor laser, Wavelength: 633 nm). The information on the fluorescence intensity of the cells was detected by side fluorescence at 90°, and the information on the side-scattered light intensity of the cells was detected by side-scattered light at 90°. As shown in FIG. 8, the leukocytes were classified into four groups corresponding to lymphocytes, monocytes, neutrophils, and eosinophils, respectively.

Example 8

A reagent kit consisting of staining agent (I) and hemolytic agent (II) was formulated with the following ingredients:

| Staining agent (I) | |
|---|---|
| Fluorescent dye F | 25.0 ppm |
| Ethylene glycol as the solvent. | |
| Hemolytic agent (II) | |
| Octyl maltoside | 0.1 g/L |
| HEPES | 20 mM |
| Potassium hydrogen phthalate | 0.5 g/L |
| Polyoxylene (21) lauryl ether | 0.9 g/L |
| 2-phenoxyl ethanol | 1.0 g/L |
| pH (adjust pH with NaOH) | 7.2 |

25 ppm of Staining agent (I) was prepared by dissolving an appropriate amount of fluorescent dye F into ethylene glycol. Following the procedure of Example 1, the hemolytic agent (II) was prepared with the above ingredients.

Figure 9:
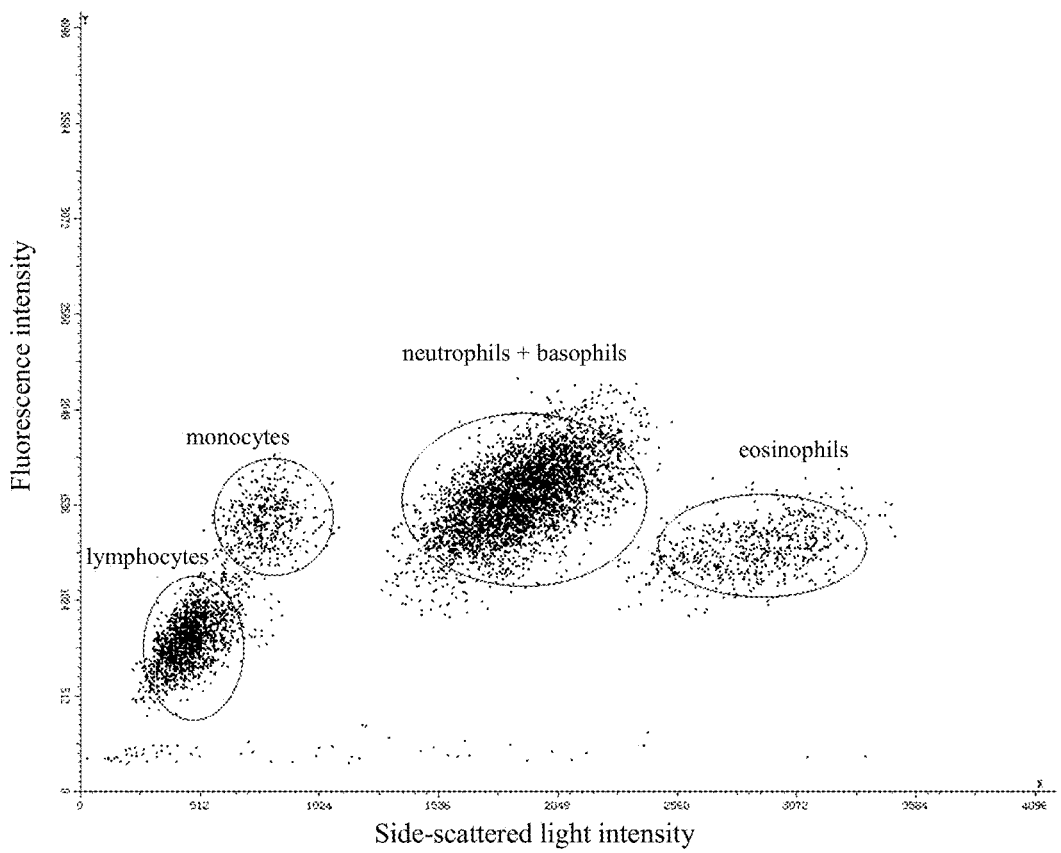
FIG. 9 is a scattergram showing the leukocyte classification obtained by the process disclosed in Example 8 of the present specification, wherein the X-axis is the intensity of side-scattered light, and the Y-axis is the intensity of fluorescence.
Figure 10:
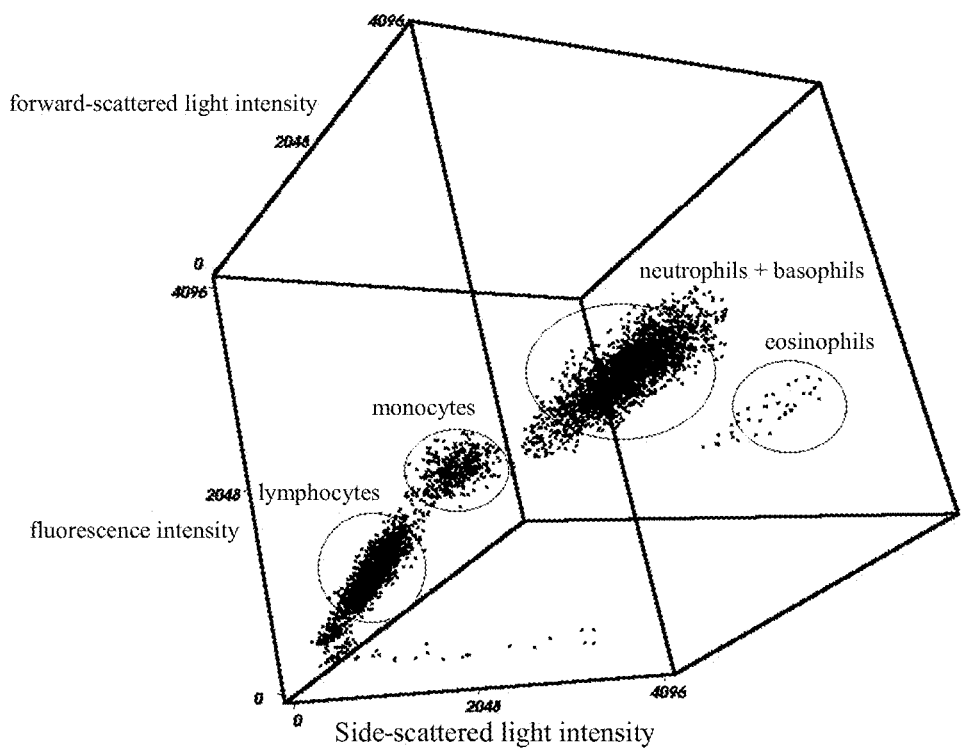
FIG. 10 is a scattergram in a three-dimensional space showing the leukocyte classification obtained by the process disclosed in Example 8 of the present specification, wherein the X-axis, Y-axis and Z-axis respectively refer to the intensity of side-scattered light, the intensity of forward-scattered light, and the intensity of fluorescence.

20 μl of the above staining agent (I) together with 20 μl of blood sample was added to 1 ml of the above hemolytic agent (II), mixed for 20 seconds while the temperature was kept at 42° C., then leukocytes were detected according to a laser flow cytometry method (Laser source: Red semiconductor laser, Wavelength: 633 nm). In order to plot a three-dimensional scattergram, the information on the fluorescence intensity of the cells was detected by side fluorescence at 90°, the information on the side-scattered light intensity of the cells was detected by side-scattered light at 90°, and the information on the forward-scattered light intensity of the cells was detected by a low angle scattered light at 1° to 5°. The classification of leukocytes in the resulting three-dimensional space is shown in FIG. 10. It is apparent from FIG. 10 that the leukocytes were classified into four groups corresponding to lymphocytes, monocytes, neutrophils, and eosinophils, respectively, and the classification between lymphocytes and monocytes is more distinct than FIG. 9.

Figure 11:
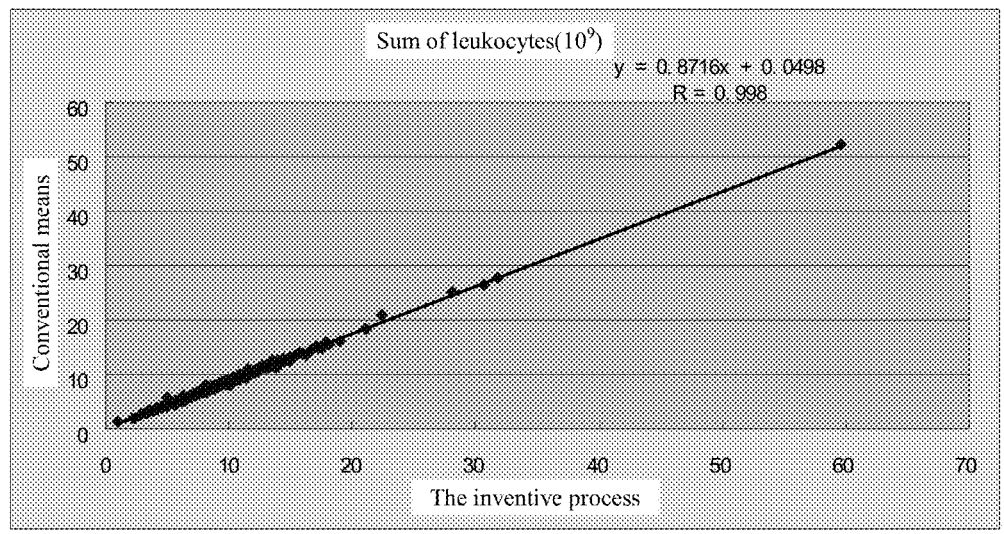
FIG. 11 shows the correlation between the sum of leukocytes obtained by the process disclosed in Example 8 of the present specification and that obtained by a conventional process (BC5500, SHENZHEN MINDRAY BIO-MEDICAL ELECTRONICS CO., LTD).
Figure 12:
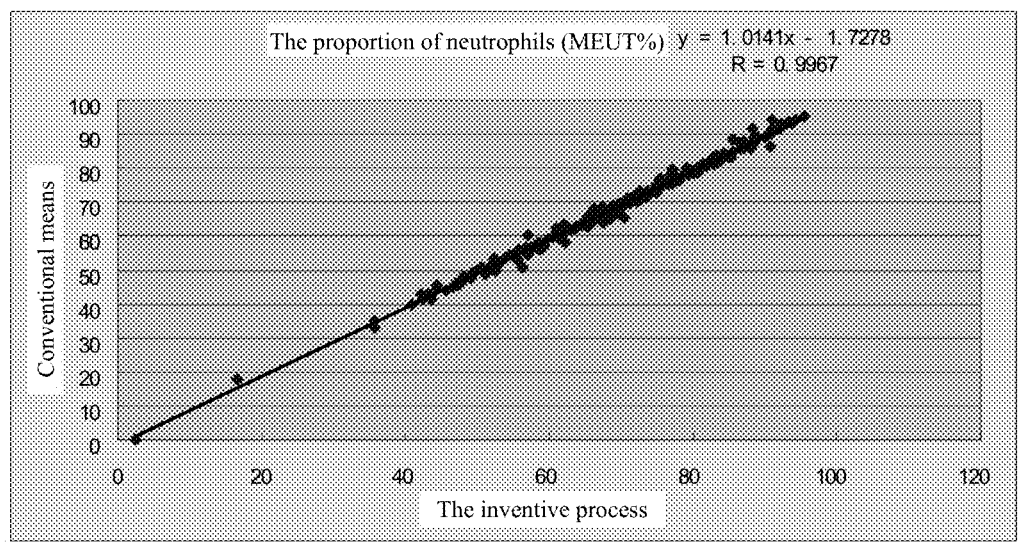
FIG. 12 shows the correlation between the proportion of neutrophils obtained by the process disclosed in Example 8 of the present specification and that obtained by a conventional process (BC5500, SHENZHEN MINDRAY BIO-MEDICAL ELECTRONICS CO., LTD).
Figure 13:
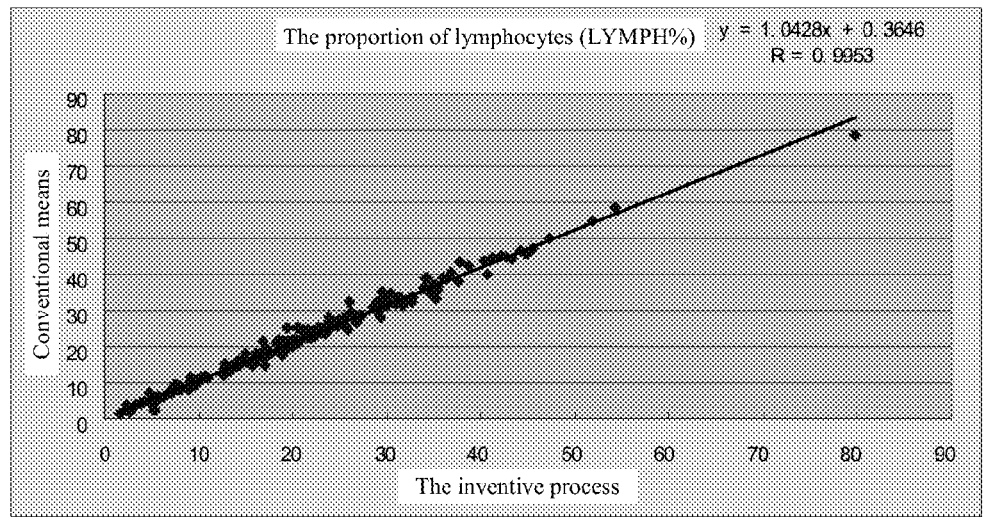
FIG. 13 shows the correlation between the proportion of lymphocytes obtained by the process disclosed in Example 8 of the present specification and that obtained by a conventional process (BC5500, SHENZHEN MINDRAY BIO-MEDICAL ELECTRONICS CO., LTD).
Figure 14:
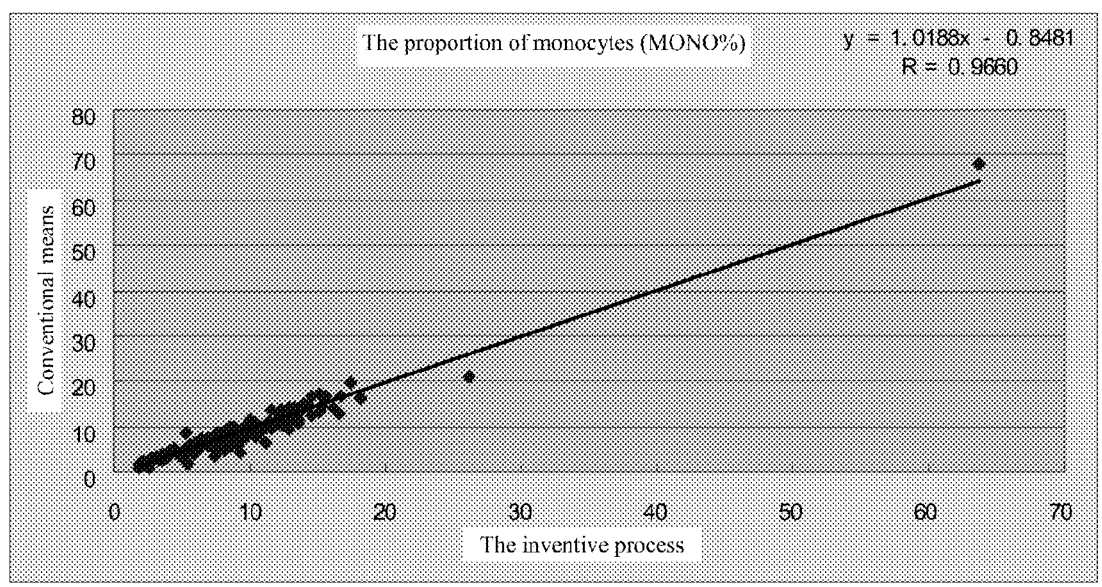
FIG. 14 shows the correlation between the proportion of monocytes obtained by the process disclosed in Example 8 of the present specification and that obtained by a conventional process (BC5500, SHENZHEN MINDRAY BIO-MEDICAL ELECTRONICS CO., LTD).
Figure 15:
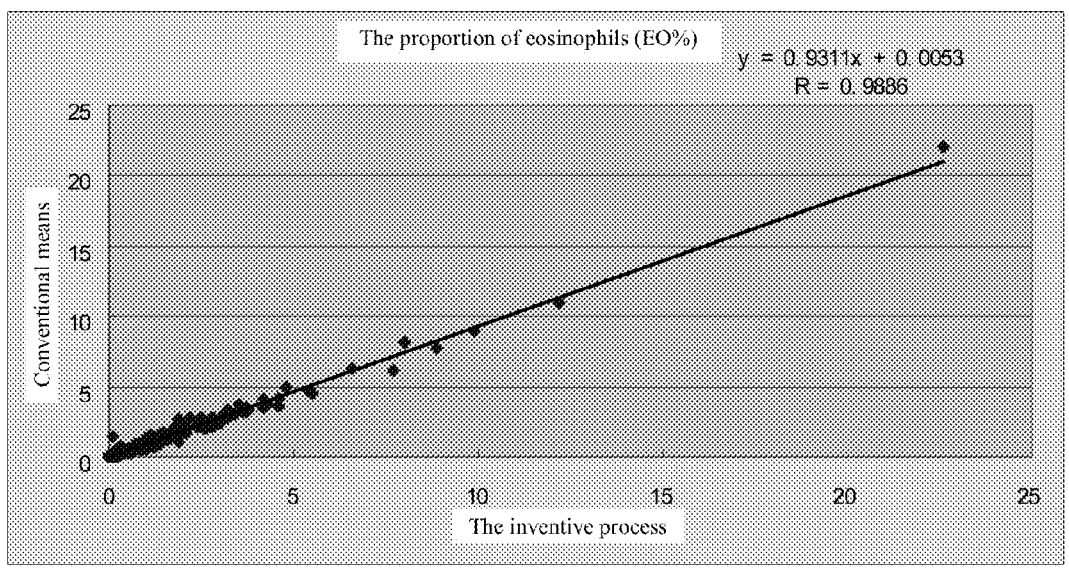
FIG. 15 shows the correlation between the proportion of eosinophils obtained by the process disclosed in Example 8 of the present specification and that obtained by a conventional process (BC5500, SHENZHEN MINDRAY BIO-MEDICAL ELECTRONICS CO., LTD).

The result of the sum of leukocytes and the proportion of each subpopulation were obtained by Example 8, and were compared with that obtained by conventional means (BC 5500, SHENZHEN MINDRAY BIO-MEDICAL ELECTRONICS CO., LTD.). The correlation is shown in FIG. 11 for the sum of leukocytes, and in FIGS. 12 to 15 for the proportion of each subpopulation of lymphocytes, i.e. monocytes, neutrophils, and eosinophils, respectively.

As shown in the aforementioned examples and drawings, leukocytes can be classified into four groups using the reagent for classifying and counting leukocytes of the present disclosure. The corresponding scattergrams show a high degree of differentiation and a better classification among each subpopulation of leukocyte, especially, lymphocytes were distinctly differentiated from the monocytes and the eosinophils were distinctly differentiated from the neutrophils. The comparison between Example 2 (FIG. 3) and Example 1 (FIG. 2) shows that the addition of a second nonionic surfactant significantly facilitates the separation of each subpopulation of leukocyte, resulting in a better differentiation. The comparison between Example 6 (FIG. 7) and Example 7 (FIG. 8) shows that the use of an alkyl glycoside makes each subpopulation of cells more concentrated in the scattergram. The comparison between Example 1 (FIG. 2) and Example 3 (FIG. 4) shows that the addition of anionic organic compound makes the cells more concentrated in the direction of fluorescence of the scattergram. The comparison between Example 7 (FIG. 8) or Example 8 (FIG. 9) and Example 4 (FIG. 5) shows that the addition of alcohols improves the differentiation.

While described in detail with reference to particular embodiments, the present disclosure is not to be construed in any case as being limited to these embodiments. It will be appreciated that various modifications may be made without departing from the spirit and scope of the disclosure as defined by the attached claims.

The invention claimed is:

1. A reagent for classifying and counting leukocytes, the reagent comprising:
   (1) a cyanine fluorescent dye;
   (2) a first nonionic surfactant that is an alkyl glycoside compound; and
   (3) a second nonionic surfactant that is other than a glycoside compound;
   wherein the reagent is configured to classify leukocytes into at least four groups, three groups corresponding to monocytes, lymphocytes and eosinophils and one group corresponding to neutrophils and basophils, by fluorescence and visible light scattering.

2. The reagent of claim 1, wherein said cyanine fluorescent dye is selected from a compound of the general formula (I), formula (II) or a combination thereof:

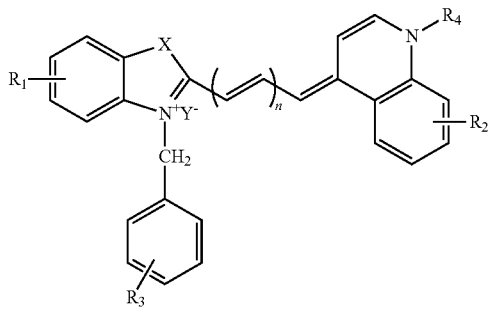

formula (I)

wherein
n is 1, 2 or 3;
X is $C(CH_3)_2$, O, S or Se;
$R_1$ and $R_2$ are each independently selected from H, $C_{1-18}$ alkyl, $C_{1-6}$ alkyl-$OR_5$ and halogen;
$R_3$ is H, $C_{1-18}$ alkyl, $OR_5$, $C_{1-6}$ alkyl-$OR_5$, $COOR_6$, $NO_2$, CN or halogen;
$R_4$ is $C_{1-18}$ alkyl, $C_{1-6}$ alkyl-$OR_5$, benzyl or halogen, wherein said benzyl is optionally substituted with one or more substituents independently selected from at least one of the following: halogen, hydroxyl, sulfhydryl, cyano, nitro, alkyl, aryl, alkoxy, haloalkyl, amino, alkylamino, amido, and carboxyl;
$R_5$ is H or $C_{1-18}$ alkyl; and
$Y^-$ is an anion;

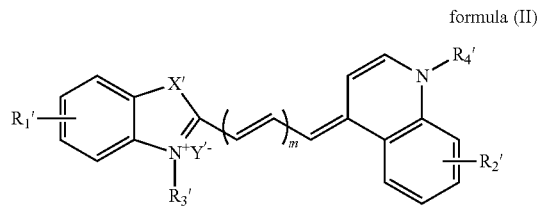

formula (II)

wherein
m is 1, 2 or 3;
X' is $C(CH_3)_2$, O, S or Se;
$R_1'$ and $R_2'$ are each independently selected from H, OH, $C_{1-18}$ alkyl, $C_{1-6}$ alkyl-$OR_5'$, $C_{1-18}$alkylsulfonate, phenyl and halogen;
$R_3'$ and $R_4'$ are each independently selected from $C_{1-18}$ alkyl-$COOR_6'$, $C_{1-18}$alkyl-$OR_6'$ and benzyl, wherein said benzyl is optionally substituted with one or more substituents independently selected from at least one of the following: halogen, hydroxyl, sulfhydryl, cyano, nitro, alkyl, aryl, alkoxy, haloalkyl, amino, alkylamino, amido, and carboxyl, provided that $R_3'$ and $R_4'$ are not simultaneously benzyl, and $R_4'$ is not $C_{1-18}$ alkyl-$OR_6'$ when $R_3'$ is benzyl;
$R_5'$ is H or $C_{1-18}$ alkyl;
$R_6'$ is H, phenyl or $C_{1-18}$ alkyl, wherein said phenyl is optionally substituted with one or more substituents independently selected from at least one of the following: halogen, hydroxyl, sulfhydryl, cyano, nitro, alkyl, aryl, alkoxy, haloalkyl, amino, alkylamino, amido, and carboxyl; and
$Y'^-$ is an anion.

3. The reagent of claim 2, wherein said compound of the general formula (I) is selected from the following compound A, compound B or compound C:

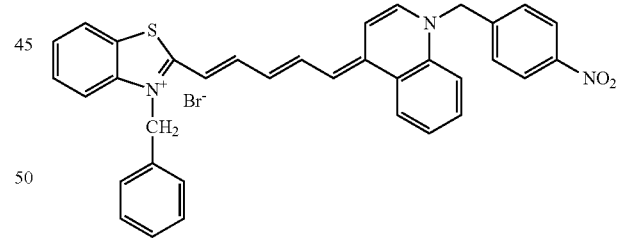

Compound A

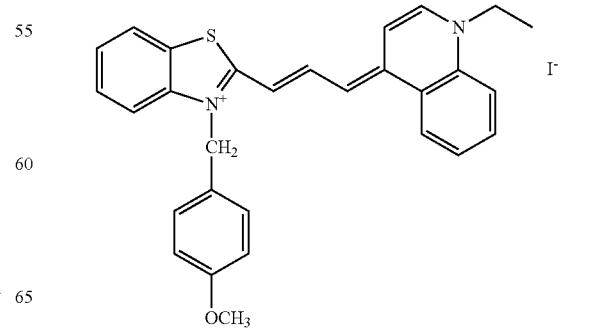

Compound B

Compound C

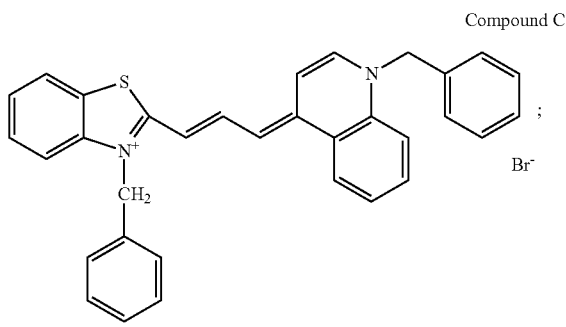

and said compound of general formula II is selected from the following compound D, compound E or compound F:

Compound D

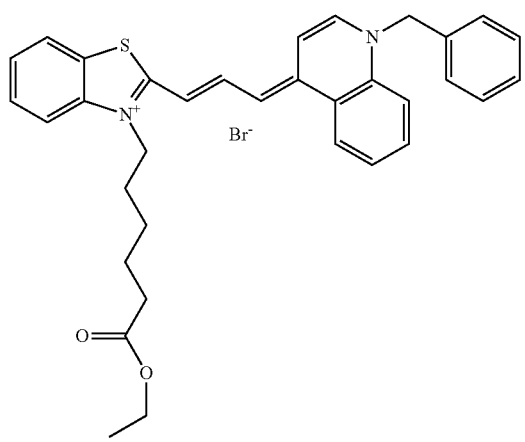

Compound E

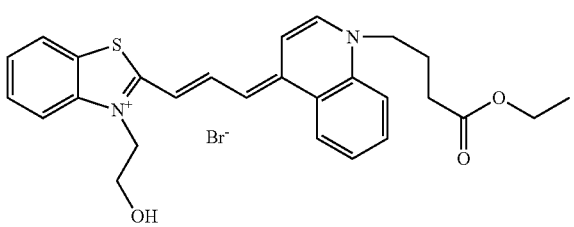

Compound F

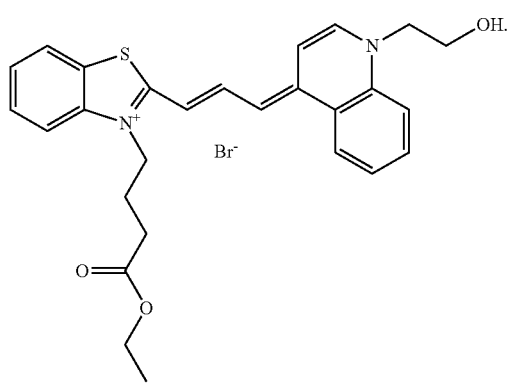

4. The reagent of claim 1, wherein the second nonionic surfactant is selected from a compound having the structure of formula (III):

$$R_1—R_2—(CH_2CH_2O)_n—H \quad \text{formula (III)}$$

wherein
$R_1$ is $C_{8-23}$ alkyl or $C_{8-23}$ alkenyl;
$R_2$ is —O—,

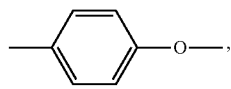

or —COO—; and
n is an integer from 10 to 30.

5. The reagent of claim 4, wherein $R_1$ is a straight-chain alkyl selected from octyl, decyl, lauryl, myristyl, cetyl or stearyl.

6. The reagent of claim 4, wherein $R_1$ is a straight-chain alkyl selected from lauryl, myristyl and cetyl.

7. The reagent of claim 4, wherein the second nonionic surfactant is selected from polyoxyethylene (15) cetyl ether, polyoxyethylene (21) lauryl ether, polyoxyethylene (23) cetyl ether, polyoxyethylene (25) cetyl ether, polyoxyethylene (30) cetyl ether, and combinations thereof.

8. The reagent of claim 1, wherein said reagent further comprises an anionic organic compound selected from an acid carrying one or more carboxyl or sulfonate groups and salts thereof.

9. The reagent of claim 8, wherein said anionic organic compound is selected from at least one of the following: formic acid, acetic acid, benzoic acid, citric acid, malic acid, phthalic acid, benzene sulfonic acid, α-naphthalene sulfonic acid, taurine, sulfobenzene sulfonic acid, and alkali metal salts thereof.

10. The reagent of claim 1, wherein the reagent further comprises an alcohol selected from at least one of the following: methanol, ethanol, ethylene glycol, isopropanol, benzyl alcohol, and 2-phenoxyl ethanol.

11. The reagent of claim 1, wherein the reagent further comprises an additional additive selected from at least one of the following: a preservative, a metal chelating agent, a buffering agent, and an osmotic regulating agent.

12. A reagent for classifying and counting leukocytes, the reagent comprising:
(1) a cyanine fluorescent dye; and
(2) an alkyl glycoside compound,
wherein the amount of glycoside compound in the reagent ranges from 0.05 g/L to 0.6 g/L, and wherein the cyanine fluorescent dye is selected from a compound of the general formula (I), formula (II) or a combination thereof:

formula (I)

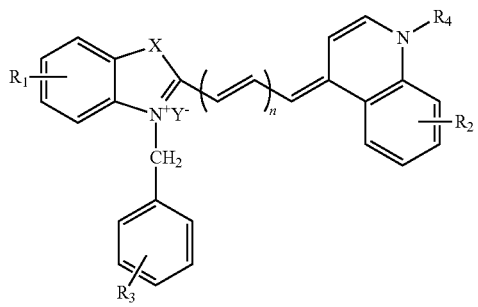

wherein n is 1, 2 or 3;

X is C(CH$_3$)$_2$, O, S or Se;

R$_1$ and R$_2$ are each independently selected from H, C$_{1-18}$ alkyl, C$_{1-6}$alkyl-OR$_5$ and halogen;

R$_3$ is H, C$_{1-18}$ alkyl, OR$_5$, C$_{1-6}$alkyl-OR$_5$, COOR$_5$, NO$_2$, CN or halogen;

R$_4$ is C$_{1-18}$ alkyl, C$_{1-6}$ alkyl-OR$_5$, benzyl or halogen, wherein said benzyl is optionally substituted with one or more substituents independently selected from at least one of the following: halogen, hydroxyl, sulfhydryl, cyano, nitro, alkyl, aryl, alkoxy, haloalkyl, amino, alkylamino, amido, and carboxyl;

R$_5$ is H or C$_{1-18}$ alkyl; and

Y$^-$ is an anion;

formula (II)

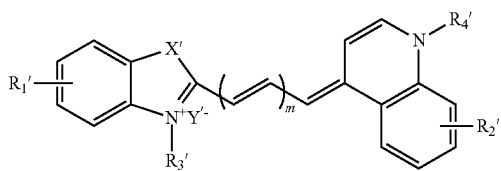

wherein m is 1, 2 or 3;

X' is C(CH$_3$)$_2$, O, S or Se;

R$_1$' and R$_2$' are each independently selected from H, OH, C$_{1-18}$ alkyl, C$_{1-6}$ alkyl-OR$_5$', C$_{1-18}$alkylsulfonate, phenyl and halogen;

R$_3$' and R$_4$' are each independently selected from C$_{1-18}$ alkyl-COOR$_6$', C$_{1-18}$ alkyl-OR$_6$' and benzyl, wherein said benzyl is optionally substituted with one or more substituents independently selected from at least one of the following: halogen, hydroxyl, sulfhydryl, cyano, nitro, alkyl, aryl, alkoxy, haloalkyl, amino, alkylamino, amido, and carboxyl, provided that R$_3$' and R$_4$' are not simultaneously benzyl, and R$_4$' is not C$_{1-18}$ alkyl-OR$_6$' when R$_3$' is benzyl;

R$_5$' is H or C$_{1-18}$ alkyl;

R$_6$' is H, phenyl or C$_{1-18}$ alkyl, wherein said phenyl is optionally substituted with one or more substituents independently selected from at least one of the following: halogen, hydroxyl, sulfhydryl, cyano, nitro, alkyl, aryl, alkoxy, haloalkyl, amino, alkylamino, amido, and carboxyl; and Y'$^-$ is an anion;

wherein the reagent is configured to classify leukocytes into at least four groups, three groups corresponding to monocytes, lymphocytes and eosinophils and one group corresponding to neutrophils and basophils, by fluorescence and visible light scattering.

* * * * *